United States Patent
Benner et al.

(10) Patent No.: US 10,059,737 B1
(45) Date of Patent: Aug. 28, 2018

(54) MOLECULAR RECOGNITION SYSTEMS WITH PYRIMIDINE ANALOG PAIRING

(71) Applicants: Steven A Benner, Gainesville, FL (US); Shuichi Hoshika, Gainesville, FL (US)

(72) Inventors: Steven A Benner, Gainesville, FL (US); Shuichi Hoshika, Gainesville, FL (US)

( * ) Notice: Subject to any disclaimer, the term of this patent is extended or adjusted under 35 U.S.C. 154(b) by 0 days.

(21) Appl. No.: 15/461,073

(22) Filed: Mar. 16, 2017

(51) Int. Cl.
*C07H 21/04* (2006.01)

(52) U.S. Cl.
CPC .................................. *C07H 21/04* (2013.01)

(58) Field of Classification Search
None
See application file for complete search history.

(56) References Cited

PUBLICATIONS

Geyer et al (Structure, vol. 11, 1485-1498, Dec. 2003) (Year: 2003).*

* cited by examiner

*Primary Examiner* — Richard A Schnizer

(57) ABSTRACT

This invention is for a new molecular recognition system, where DNA-like molecules comprising segments built from nucleotides that carry only a small which comprises process by which one molecule interacts with a specific second molecule, or by which a portion of a single molecule interacts specifically with another portion of the same molecule. Further, this invention relates to molecular recognition that follows simple rules. Further, this invention relates to molecular systems that are linear biopolymers that are analogs of DNA and RNA, in that they are built from a small set of building blocks that are linked together by phosphate groups, where the building blocks comprise a sugar (ribose, 2'-deoxyribose, or an analog) attached to a heterocycle. The molecular recognition that they display differs from that displayed by DNA and RNA, in that the rules governing molecular recognition break the rules of size complementarity followed in molecular recognition displayed between and within strands of DNA and RNA.

3 Claims, 9 Drawing Sheets

Figure 1:
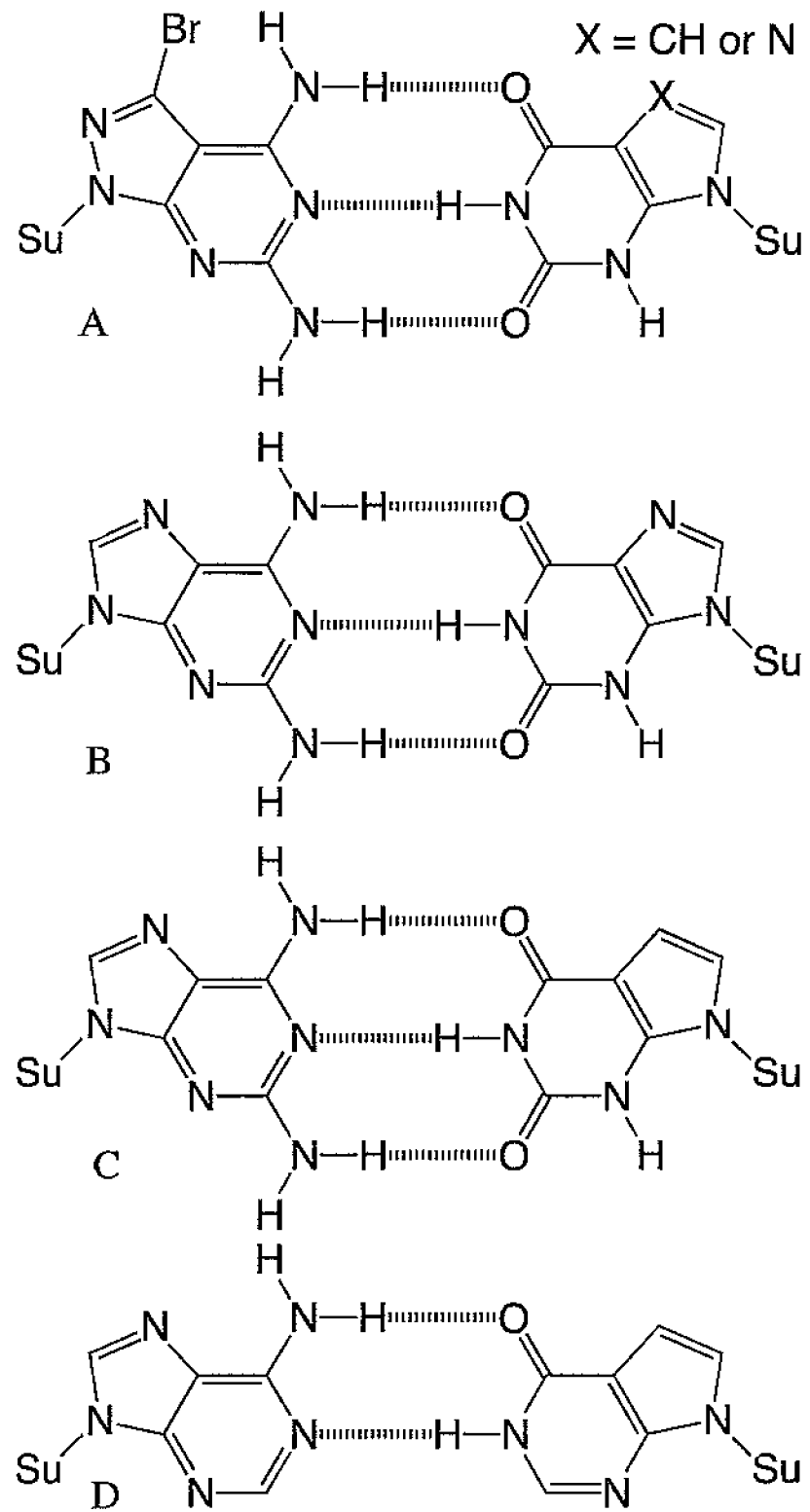

Specification includes a Sequence Listing.

A

B

SEQUENCE LISTING

<160> NUMBER OF SEQ ID NOS: 50

<210> SEQ ID NO 1
<211> LENGTH: 15
<212> TYPE: DNA
<213> ORGANISM: Artificial Sequence
<220> FEATURE:
<223> OTHER INFORMATION: Synthetic

<400> SEQUENCE: 1
cgtcgccccc ggctc            15

<210> SEQ ID NO 2
<211> LENGTH: 15
<212> TYPE: DNA
<213> ORGANISM: Artificial Sequence
<220> FEATURE:
<223> OTHER INFORMATION: Synthetic

<400> SEQUENCE: 2
gagccggggg cgacg            15

<210> SEQ ID NO 3
<211> LENGTH: 15
<212> TYPE: DNA
<213> ORGANISM: Artificial Sequence
<220> FEATURE:
<223> OTHER INFORMATION: Synthetic

<400> SEQUENCE: 3
cgtcgttttt ggctc            15

<210> SEQ ID NO 4
<211> LENGTH: 15
<212> TYPE: DNA
<213> ORGANISM: Artificial Sequence
<220> FEATURE:
<223> OTHER INFORMATION: Synthetic

<400> SEQUENCE: 4
gagccaaaaa cgacg            15

<210> SEQ ID NO 5
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: 7-amino-9-(1'-beta-D-2'-deoxyribofuranosyl)-
      imidazo[1,2-c]pyrimidin-5(1H)-one

<400> SEQUENCE: 5
cgtcgttntt ggctc            15

<210> SEQ ID NO 6
<211> LENGTH: 15

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: 6-amino-3-(2'-deoxy-D-ribofuranosyl)-5-nitro-
      1H-pyridin-2-one

<400> SEQUENCE: 6
gagccaanaa cgacg                                                    15

<210> SEQ ID NO 7
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(9)
<223> OTHER INFORMATION: 7-amino-9-(1'-beta-D-2'-deoxyribofuranosyl)-
      imidazo[1,2-c]pyrimidin-5(1H)-one

<400> SEQUENCE: 7
cgtcgtnnnt ggctc                                                    15

<210> SEQ ID NO 8
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(9)
<223> OTHER INFORMATION: 6-amino-3-(2'-deoxy-D-ribofuranosyl)-5-nitro-
      1H-pyridin-2-one

<400> SEQUENCE: 8
gagccannna cgacg                                                    15

<210> SEQ ID NO 9
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (8)..(8)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (10)..(10)
<223> OTHER INFORMATION: 7-amino-9-(1'-beta-D-2'-deoxyribofuranosyl)-
      imidazo[1,2-c]pyrimidin-5(1H)-one

<400> SEQUENCE: 9
cgtcgntntn ggctc                                                    15

<210> SEQ ID NO 10
<211> LENGTH: 15
<212> TYPE: DNA
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 6-amino-3-(2'-deoxy-D-ribofuranosyl)-5-nitro-
      1H-pyridin-2-one
<220> FEATURE:
<221> NAME/KEY: misc_feature
<222> LOCATION: (8)..(8)
<223> OTHER INFORMATION: 6-amino-3-(2'-deoxy-D-ribofuranosyl)-5-nitro-
      1H-pyridin-2-one
<220> FEATURE:
<221> NAME/KEY: misc_feature
<222> LOCATION: (10)..(10)
<223> OTHER INFORMATION: 6-amino-3-(2'-deoxy-D-ribofuranosyl)-5-nitro-
      1H-pyridin-2-one

<400> SEQUENCE: 10
gagccnanan cgacg                                                   15

<210> SEQ ID NO 11
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: 7-amino-9-(1'-beta-D-2'-deoxyribofuranosyl)-
      imidazo[1,2-c]pyrimidin-5(1H)-one

<400> SEQUENCE: 11
cgtcgnnnnn ggctc                                                   15

<210> SEQ ID NO 12
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: 6-amino-3-(2'-deoxy-D-ribofuranosyl)-5-nitro-
      1H-pyridin-2-one

<400> SEQUENCE: 12
gagccnnnnn cgacg                                                   15

<210> SEQ ID NO 13
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: 4-amino-N1-methyl-5-(1'-beta-D-2'-
      deoxyribofuranosyl)-2(1H)-pyrimidinone

<400> SEQUENCE: 13
cgtcgttntt ggctc                                                   15

<210> SEQ ID NO 14
<211> LENGTH: 15
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (8)..(8)
<223> OTHER INFORMATION: 4-amino-3-hydro-7-(2-deoxy-beta-D-
      ribofuranosyl)-pyrrolo[2,3-d]pyrimidin-2-one

<400> SEQUENCE: 14
gagccaanaa cgacg                                                    15

<210> SEQ ID NO 15
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(9)
<223> OTHER INFORMATION: 4-amino-N1-methyl-5-(1'-beta-D-2'-
      deoxyribofuranosyl)-2(1H)-pyrimidinone

<400> SEQUENCE: 15
cgtcgtnnnt ggctc                                                    15

<210> SEQ ID NO 16
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(9)
<223> OTHER INFORMATION: 4-amino-3-hydro-7-(2-deoxy-beta-D-
      ribofuranosyl)-pyrrolo[2,3-d]pyrimidin-2-one

<400> SEQUENCE: 16
gagccannna cgacg                                                    15

<210> SEQ ID NO 17
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 4-amino-N1-methyl-5-(1'-beta-D-2'-
      deoxyribofuranosyl)-2(1H)-pyrimidinone
<220> FEATURE:
<221> NAME/KEY: misc_feature
<222> LOCATION: (8)..(8)
<223> OTHER INFORMATION: 4-amino-N1-methyl-5-(1'-beta-D-2'-
      deoxyribofuranosyl)-2(1H)-pyrimidinone
<220> FEATURE:
<221> NAME/KEY: misc_feature
<222> LOCATION: (10)..(10)
<223> OTHER INFORMATION: 4-amino-N1-methyl-5-(1'-beta-D-2'-
      deoxyribofuranosyl)-2(1H)-pyrimidinone

<400> SEQUENCE: 17
cgtcgntntn ggctc                                                    15

<210> SEQ ID NO 18
<211> LENGTH: 15
<212> TYPE: DNA
<213> ORGANISM: Artificial Sequence
<220> FEATURE:
```

```
<223> OTHER INFORMATION: Synthetic
<220> FEATURE:
<221> NAME/KEY: misc_feature
<222> LOCATION: (6)..(6)
<223> OTHER INFORMATION: 4-amino-3-hydro-7-(2-deoxy-beta-D-
      ribofuranosyl)-pyrrolo[2,3-d]pyrimidin-2-one
<220> FEATURE:
<221> NAME/KEY: misc_feature
<222> LOCATION: (8)..(8)
<223> OTHER INFORMATION: 4-amino-3-hydro-7-(2-deoxy-beta-D-
      ribofuranosyl)-pyrrolo[2,3-d]pyrimidin-2-one
<220> FEATURE:
<221> NAME/KEY: misc_feature
<222> LOCATION: (10)..(10)
<223> OTHER INFORMATION: 4-amino-3-hydro-7-(2-deoxy-beta-D-
      ribofuranosyl)-pyrrolo[2,3-d]pyrimidin-2-one

<400> SEQUENCE: 18
gagccnanan cgacg                                                      15

<210> SEQ ID NO 19
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: 4-amino-N1-methyl-5-(1'-beta-D-2'-
      deoxyribofuranosyl)-2(1H)-pyrimidinone

<400> SEQUENCE: 19
cgtcgnnnnn ggctc                                                      15

<210> SEQ ID NO 20
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: 4-amino-3-hydro-7-(2-deoxy-beta-D-
      ribofuranosyl)-pyrrolo[2,3-d]pyrimidin-2-one

<400> SEQUENCE: 20
gagccnnnnn cgacg                                                      15

<210> SEQ ID NO 21
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: 2'-deoxy-7-deazaxanthosine

<400> SEQUENCE: 21
cgtcgttntt ggctc                                                      15

<210> SEQ ID NO 22
<211> LENGTH: 15
<212> TYPE: DNA
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (8)..(8)
<223> OTHER INFORMATION: 2,6-diamino-3-nitro-5-(1'-beta-D-2'-
      deoxyribofuranosyl)-pyridine

<400> SEQUENCE: 22
gagccaanaa cgacg                                                    15

<210> SEQ ID NO 23
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(9)
<223> OTHER INFORMATION: 2'-deoxy-7-deazaxanthosine

<400> SEQUENCE: 23
cgtcgtnnnt ggctc                                                    15

<210> SEQ ID NO 24
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(9)
<223> OTHER INFORMATION: 2,6-diamino-3-nitro-5-(1'-beta-D-2'-
      deoxyribofuranosyl)-pyridine

<400> SEQUENCE: 24
gagccannna cgacg                                                    15

<210> SEQ ID NO 25
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 2'-deoxy-7-deazaxanthosine
<220> FEATURE:
<221> NAME/KEY: misc_feature
<222> LOCATION: (8)..(8)
<223> OTHER INFORMATION: 2'-deoxy-7-deazaxanthosine
<220> FEATURE:
<221> NAME/KEY: misc_feature
<222> LOCATION: (10)..(10)
<223> OTHER INFORMATION: 2'-deoxy-7-deazaxanthosine

<400> SEQUENCE: 25
cgtcgntntn ggctc                                                    15

<210> SEQ ID NO 26
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 2,6-diamino-3-nitro-5-(1'-beta-D-2'-
      deoxyribofuranosyl)-pyridin
<220> FEATURE:
```

```
<221> NAME/KEY: misc_feature
<222> LOCATION: (8)..(8)
<223> OTHER INFORMATION: 2,6-diamino-3-nitro-5-(1'-beta-D-2'-
      deoxyribofuranosyl)-pyridin
<220> FEATURE:
<221> NAME/KEY: misc_feature
<222> LOCATION: (10)..(10)
<223> OTHER INFORMATION: 2,6-diamino-3-nitro-5-(1'-beta-D-2'-
      deoxyribofuranosyl)-pyridin

<400> SEQUENCE: 26
gagccnanan cgacg                                                    15

<210> SEQ ID NO 27
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: 2'-deoxy-7-deazaxanthosine

<400> SEQUENCE: 27
cgtcgnnnnn ggctc                                                    15

<210> SEQ ID NO 28
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: 2,6-diamino-3-nitro-5-(1'-beta-D-2'-
      deoxyribofuranosyl)-pyridine

<400> SEQUENCE: 28
gagccnnnnn cgacg                                                    15

<210> SEQ ID NO 29
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: 8-(beta-D-2'-deoxyribofuranosyl)imidazo[1,2-a]-
      1,3,5-triazine-2(8H)-4(3H)-dione

<400> SEQUENCE: 29
cgtcgttntt ggctc                                                    15

<210> SEQ ID NO 30
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: 2,4-diamino-5-(1'-beta-D-2'-
      deoxyribofuranosyl)-pyrimidine

<400> SEQUENCE: 30
```
gagccaanaa cgacg                                                         15

<210> SEQ ID NO 31
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: 2'-deoxyxanthosine

<400> SEQUENCE: 31
cgtcgttntt ggctc                                                         15

<210> SEQ ID NO 32
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(9)
<223> OTHER INFORMATION: 8-(beta-D-2'-deoxyribofuranosyl)imidazo[1,2-a]-
      1,3,5-triazine-2(8H)-4(3H)-dione

<400> SEQUENCE: 32
cgtcgtnnnt ggctc                                                         15

<210> SEQ ID NO 33
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(9)
<223> OTHER INFORMATION: 2,4-diamino-5-(1'-beta-D-2'-
      deoxyribofuranosyl)-pyrimidine

<400> SEQUENCE: 33
gagccannna cgacg                                                         15

<210> SEQ ID NO 34
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(9)
<223> OTHER INFORMATION: 2'-deoxyxanthosine

<400> SEQUENCE: 34
cgtcgtnnnt ggctc                                                         15

<210> SEQ ID NO 35
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 8-(beta-D-2'-deoxyribofuranosyl)imidazo[1,2-a]-

```
            1,3,5-triazine-2(8H)-4(3H)-dione
<220> FEATURE:
<221> NAME/KEY: misc_feature
<222> LOCATION: (8)..(8)
<223> OTHER INFORMATION: 8-(beta-D-2'-deoxyribofuranosyl)imidazo[1,2-a]-
      1,3,5-triazine-2(8H)-4(3H)-dione
<220> FEATURE:
<221> NAME/KEY: misc_feature
<222> LOCATION: (10)..(10)
<223> OTHER INFORMATION: 8-(beta-D-2'-deoxyribofuranosyl)imidazo[1,2-a]-
      1,3,5-triazine-2(8H)-4(3H)-dione

<400> SEQUENCE: 35
cgtcgntntn ggctc                                                    15

<210> SEQ ID NO 36
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 2,4-diamino-5-(1'-beta-D-2'-
      deoxyribofuranosyl)-pyrimidine
<220> FEATURE:
<221> NAME/KEY: misc_feature
<222> LOCATION: (8)..(8)
<223> OTHER INFORMATION: 2,4-diamino-5-(1'-beta-D-2'-
      deoxyribofuranosyl)-pyrimidine
<220> FEATURE:
<221> NAME/KEY: misc_feature
<222> LOCATION: (10)..(10)
<223> OTHER INFORMATION: 2,4-diamino-5-(1'-beta-D-2'-
      deoxyribofuranosyl)-pyrimidine

<400> SEQUENCE: 36
gagccnanan cgacg                                                    15

<210> SEQ ID NO 37
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 2'-deoxyxanthosine
<220> FEATURE:
<221> NAME/KEY: misc_feature
<222> LOCATION: (8)..(8)
<223> OTHER INFORMATION: 2'-deoxyxanthosine
<220> FEATURE:
<221> NAME/KEY: misc_feature
<222> LOCATION: (10)..(10)
<223> OTHER INFORMATION: 2'-deoxyxanthosine

<400> SEQUENCE: 37
cgtcgntntn ggctc                                                    15

<210> SEQ ID NO 38
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: 8-(beta-D-2'-deoxyribofuranosyl)imidazo[1,2-a]-
      1,3,5-triazine-2(8H)-4(3H)-dione
```

<400> SEQUENCE: 38
cgtcgnnnnn ggctc                                                          15

<210> SEQ ID NO 39
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: 2,4-diamino-5-(1'-beta-D-2'-
      deoxyribofuranosyl)-pyrimidine

<400> SEQUENCE: 39
gagccnnnnn cgacg                                                          15

<210> SEQ ID NO 40
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: 2'-deoxyxanthosine

<400> SEQUENCE: 40
cgtcgnnnnn ggctc                                                          15

<210> SEQ ID NO 41
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 6-amino-3-(2'-deoxy-D-ribofuranosyl)-5-nitro-
      1H-pyridin-2-one
<220> FEATURE:
<221> NAME/KEY: misc_feature
<222> LOCATION: (7)..(7)
<223> OTHER INFORMATION: 2,6-diamino-3-nitro-5-(1'-beta-D-2'-
      deoxyribofuranosyl)-pyridine
<220> FEATURE:
<221> NAME/KEY: misc_feature
<222> LOCATION: (8)..(8)
<223> OTHER INFORMATION: 6-amino-3-(2'-deoxy-D-ribofuranosyl)-5-nitro-
      1H-pyridin-2-one
<220> FEATURE:
<221> NAME/KEY: misc_feature
<222> LOCATION: (9)..(9)
<223> OTHER INFORMATION: 2,6-diamino-3-nitro-5-(1'-beta-D-2'-
      deoxyribofuranosyl)-pyridine
<220> FEATURE:
<221> NAME/KEY: misc_feature
<222> LOCATION: (10)..(10)
<223> OTHER INFORMATION: 6-amino-3-(2'-deoxy-D-ribofuranosyl)-5-nitro-
      1H-pyridin-2-one

<400> SEQUENCE: 41
gagccnnnnn cgacg                                                          15

<210> SEQ ID NO 42
<211> LENGTH: 15
<212> TYPE: DNA

```
<213> ORGANISM: Artificial Sequence
<220> FEATURE:
<223> OTHER INFORMATION: Synthetic

<400> SEQUENCE: 42
gagccttttt cgacg                                                    15

<210> SEQ ID NO 43
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2,6-diamino-3-nitro-5-(1'-beta-D-2'-
      deoxyribofuranosyl)-pyridine
<220> FEATURE:
<221> NAME/KEY: misc_feature
<222> LOCATION: (2)..(3)
<223> OTHER INFORMATION: 6-amino-3-(2'-deoxy-D-ribofuranosyl)-5-nitro-
      1H-pyridin-2-one
<220> FEATURE:
<221> NAME/KEY: misc_feature
<222> LOCATION: (5)..(5)
<223> OTHER INFORMATION: 6-amino-3-(2'-deoxy-D-ribofuranosyl)-5-nitro-
      1H-pyridin-2-one
<220> FEATURE:
<221> NAME/KEY: misc_feature
<222> LOCATION: (6)..(6)
<223> OTHER INFORMATION: 4-amino-N1-methyl-5-(1'-beta-D-2'-
      deoxyribofuranosyl)-2(1H)-pyrimidinone
<220> FEATURE:
<221> NAME/KEY: misc_feature
<222> LOCATION: (7)..(7)
<223> OTHER INFORMATION: 2,6-diamino-3-nitro-5-(1'-beta-D-2'-
      deoxyribofuranosyl)-pyridine
<220> FEATURE:
<221> NAME/KEY: misc_feature
<222> LOCATION: (10)..(11)
<223> OTHER INFORMATION: 2,6-diamino-3-nitro-5-(1'-beta-D-2'-
      deoxyribofuranosyl)-pyridine
<220> FEATURE:
<221> NAME/KEY: misc_feature
<222> LOCATION: (12)..(12)
<223> OTHER INFORMATION: 4-amino-N1-methyl-5-(1'-beta-D-2'-
      deoxyribofuranosyl)-2(1H)-pyrimidinone
<220> FEATURE:
<221> NAME/KEY: misc_feature
<222> LOCATION: (14)..(14)
<223> OTHER INFORMATION: 4-amino-N1-methyl-5-(1'-beta-D-2'-
      deoxyribofuranosyl)-2(1H)-pyrimidinone

<400> SEQUENCE: 43
nnntnnnttn nntnt                                                    15

<210> SEQ ID NO 44
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-deoxy-2-aminoadenosine
<220> FEATURE:
<221> NAME/KEY: misc_feature
<222> LOCATION: (2)..(2)
<223> OTHER INFORMATION: 4-amino-3-hydro-7-(2-deoxy-beta-D-
      ribofuranosyl)-pyrrolo[2,3-d]pyrimidin-2-one
<220> FEATURE:
<221> NAME/KEY: misc_feature
<222> LOCATION: (3)..(3)
```

```
<223> OTHER INFORMATION: 2'-deoxy-2-aminoadenosine
<220> FEATURE:
<221> NAME/KEY: misc_feature
<222> LOCATION: (4)..(4)
<223> OTHER INFORMATION: 4-amino-3-hydro-7-(2-deoxy-beta-D-
      ribofuranosyl)-pyrrolo[2,3-d]pyrimidin-2-one
<220> FEATURE:
<221> NAME/KEY: misc_feature
<222> LOCATION: (5)..(6)
<223> OTHER INFORMATION: 2'-deoxy-7-deazaxanthosine
<220> FEATURE:
<221> NAME/KEY: misc_feature
<222> LOCATION: (7)..(8)
<223> OTHER INFORMATION: 2'-deoxy-2-aminoadenosine
<220> FEATURE:
<221> NAME/KEY: misc_feature
<222> LOCATION: (9)..(9)
<223> OTHER INFORMATION: 2'-deoxy-7-deazaxanthosine
<220> FEATURE:
<221> NAME/KEY: misc_feature
<222> LOCATION: (10)..(10)
<223> OTHER INFORMATION: 4-amino-3-hydro-7-(2-deoxy-beta-D-
      ribofuranosyl)-pyrrolo[2,3-d]pyrimidin-2-one
<220> FEATURE:
<221> NAME/KEY: misc_feature
<222> LOCATION: (11)..(11)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (12)..(12)
<223> OTHER INFORMATION: 2'-deoxy-2-aminoadenosine
<220> FEATURE:
<221> NAME/KEY: misc_feature
<222> LOCATION: (13)..(14)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (15)..(15)
<223> OTHER INFORMATION: 2'-deoxy-7-deazaxanthosine

<400> SEQUENCE: 44
nnnnnnnnnn nnnnn                                               15

<210> SEQ ID NO 45
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-deoxy-2-aminoadenosine
<220> FEATURE:
<221> NAME/KEY: misc_feature
<222> LOCATION: (2)..(3)
<223> OTHER INFORMATION: 4-amino-3-hydro-7-(2-deoxy-beta-D-
      ribofuranosyl)-pyrrolo[2,3-d]pyrimidin-2-one
<220> FEATURE:
<221> NAME/KEY: misc_feature
<222> LOCATION: (4)..(4)
<223> OTHER INFORMATION: 2'-deoxy-7-deazaxanthosine
<220> FEATURE:
<221> NAME/KEY: misc_feature
<222> LOCATION: (5)..(5)
<223> OTHER INFORMATION: 4-amino-3-hydro-7-(2-deoxy-beta-D-
      ribofuranosyl)-pyrrolo[2,3-d]pyrimidin-2-one
<220> FEATURE:
<221> NAME/KEY: misc_feature
<222> LOCATION: (6)..(6)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (7)..(7)
```

```
<223> OTHER INFORMATION: 2'-deoxy-2-aminoadenosine
<220> FEATURE:
<221> NAME/KEY: misc_feature
<222> LOCATION: (8)..(9)
<223> OTHER INFORMATION: 2'-deoxy-7-deazaxanthosine
<220> FEATURE:
<221> NAME/KEY: misc_feature
<222> LOCATION: (10)..(11)
<223> OTHER INFORMATION: 2'-deoxy-2-aminoadenosine
<220> FEATURE:
<221> NAME/KEY: misc_feature
<222> LOCATION: (12)..(12)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (13)..(13)
<223> OTHER INFORMATION: 2'-deoxy-7-deazaxanthosine
<220> FEATURE:
<221> NAME/KEY: misc_feature
<222> LOCATION: (14)..(14)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (15)..(15)
<223> OTHER INFORMATION: 2'-deoxy-7-deazaxanthosine

<400> SEQUENCE: 45
nnnnnnnnnn nnnnn                                                  15

<210> SEQ ID NO 46
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2,6-diamino-3-nitro-5-(1'-beta-D-2'-
      deoxyribofuranosyl)-pyridine
<220> FEATURE:
<221> NAME/KEY: misc_feature
<222> LOCATION: (2)..(2)
<223> OTHER INFORMATION: 6-amino-3-(2'-deoxy-D-ribofuranosyl)-5-nitro-
      1H-pyridin-2-one
<220> FEATURE:
<221> NAME/KEY: misc_feature
<222> LOCATION: (3)..(3)
<223> OTHER INFORMATION: 2,6-diamino-3-nitro-5-(1'-beta-D-2'-
      deoxyribofuranosyl)-pyridine
<220> FEATURE:
<221> NAME/KEY: misc_feature
<222> LOCATION: (4)..(4)
<223> OTHER INFORMATION: 6-amino-3-(2'-deoxy-D-ribofuranosyl)-5-nitro-
      1H-pyridin-2-one
<220> FEATURE:
<221> NAME/KEY: misc_feature
<222> LOCATION: (7)..(8)
<223> OTHER INFORMATION: 2,6-diamino-3-nitro-5-(1'-beta-D-2'-
      deoxyribofuranosyl)-pyridine
<220> FEATURE:
<221> NAME/KEY: misc_feature
<222> LOCATION: (10)..(10)
<223> OTHER INFORMATION: 6-amino-3-(2'-deoxy-D-ribofuranosyl)-5-nitro-
      1H-pyridin-2-one
```

```
<220> FEATURE:
<221> NAME/KEY: misc_feature
<222> LOCATION: (11)..(11)
<223> OTHER INFORMATION: 4-amino-N1-methyl-5-(1'-beta-D-2'-
      deoxyribofuranosyl)-2(1H)-pyrimidinone
<220> FEATURE:
<221> NAME/KEY: misc_feature
<222> LOCATION: (12)..(12)
<223> OTHER INFORMATION: 2,6-diamino-3-nitro-5-(1'-beta-D-2'-
      deoxyribofuranosyl)-pyridine
<220> FEATURE:
<221> NAME/KEY: misc_feature
<222> LOCATION: (13)..(14)
<223> OTHER INFORMATION: 4-amino-N1-methyl-5-(1'-beta-D-2'-
      deoxyribofuranosyl)-2(1H)-pyrimidinone

<400> SEQUENCE: 46
nnnnttnntn nnnnt                                                      15

<210> SEQ ID NO 47
<211> LENGTH: 15
<212> TYPE: DNA
<213> ORGANISM: Artificial Sequence
<220> FEATURE:
<223> OTHER INFORMATION: Synthetic

<400> SEQUENCE: 47
agagaaaaag gagga                                                      15

<210> SEQ ID NO 48
<211> LENGTH: 15
<212> TYPE: DNA
<213> ORGANISM: Artificial Sequence
<220> FEATURE:
<223> OTHER INFORMATION: Synthetic

<400> SEQUENCE: 48
tcctcctttt tctct                                                      15

<210> SEQ ID NO 49
<211> LENGTH: 15
<212> TYPE: DNA
<213> ORGANISM: Artificial Sequence
<220> FEATURE:
<223> OTHER INFORMATION: Synthetic

<400> SEQUENCE: 49
aggaggaaaa agaga                                                      15

<210> SEQ ID NO 50
<211> LENGTH: 15
<212> TYPE: DNA
<213> ORGANISM: Artificial Sequence
<220> FEATURE:
<223> OTHER INFORMATION: Synthetic

<400> SEQUENCE: 50 tctcttttc ctcct                                                       15
```

MOLECULAR RECOGNITION SYSTEMS WITH PYRIMIDINE ANALOG PAIRING

STATEMENT OF RIGHTS TO INVENTIONS MADE UNDER FEDERALLY SPONSORED RESEARCH

This invention was made with government support under NNX14AK37G, awarded by the National Aeronautics and Space Administration. The government has certain rights in the invention.

CROSS REFERENCE TO RELATED APPLICATIONS

None

THE NAMES OF THE PARTIES TO A JOINT RESEARCH AGREEMENT

Not applicable

INCORPORATION-BY-REFERENCE OF MATERIAL SUBMITTED ON A COMPACT DISC

None

BACKGROUND OF THE INVENTION

(1) Field of the Invention

The field of this invention is molecular recognition, which comprises a process by which one molecule interacts with a specific second molecule, or by which a portion of a single molecule interacts with another specific portion of the same molecule. This invention relates to molecular recognition that follows simple rules, and where the species being recognized are analogs of DNA and RNA, in that they are built from a small set of building blocks that are linked together by phosphate diester groups, and where the building blocks comprise a sugar (ribose, 2'-deoxyribose, or an analog) attached to a heterocycle. The molecular recognition rules that they follow differ, however, from the rules followed by DNA and RNA, in that the rules governing the molecular recognition of the instant invention break the rules of size complementarity followed in molecular recognition between and within strands of DNA and RNA.

(2) Description of Related Art

Molecular technology frequently requires that molecules bind specifically to other molecules. One well-known example of specific molecular interactions occurs in crystallization, where a macroscopic structure is formed by the self-assembly of multiple copies of the same molecule or molecular system. This type of molecular interaction is quite specific, with crystallization often used to purify compositions of matter so they are homogeneous. Molecular interactions may also be nonspecific, as in the precipitation of proteins from eggs upon cooking.

Only rarely, however, does molecular recognition follow simple rules. The archetypal example of rule-based molecular recognition is displayed by nucleic acids, DNA and RNA. Here, an oligonucleotide or oligonucleotide analog binds in an anti-parallel orientation to a complementary oligonucleotide according to Watson and Crick rules of nucleobase pairing. Those rules pair adenine (A) (or 2-aminoadenine) with thymine (T) (or uracil, U), and pair guanine (G) with cytosine (C), with complementary strands anti-parallel to one another. The same rules describe the molecular interaction observed when a segment of a single oligonucleotide molecule interacts with another segment of the same oligonucleotide, for example, to form a hairpin.

These Watson-Crick pairing rules are understood in the art to be the consequence of two molecular principles of complementarity. The first is size complementarity. Here, molecular recognition is taught to require that a large purine nucleobase on one of the two interacting oligonucleotides pair with a small pyrimidine nucleobase on the other.

The second rule is hydrogen bonding complementarity, where hydrogen bonding donors on one of the two interacting moieties match with hydrogen bonding acceptors on the other. In DNA and RNA, hydrogen bond donors are heteroatoms (nitrogen or oxygen) bearing a hydrogen, while hydrogen bond acceptors are heteroatoms (nitrogen or oxygen) with unshared electrons.

In natural DNA and RNA, these rules of molecular recognition are implemented using standard pyrimidines, thymine (or uracil) and cytosine, all having a six membered ring, and standard purines (adenine and guanine), a ring system composed of a fused five-six ring system. In both cases, a middle hydrogen bonding moiety allows the two ring systems to interact. Additional functional groups appended to each of the ring systems provide hydrogen bonding moieties on either side of the central hydrogen bond. The A:T nucleobase pair uses this hydrogen bonding pattern only partly; it is completely used in the 2-aminoA:T base pair.

The art teaches that size complementarity is more important than hydrogen bonding complementarity [Goodman, M. F. (1999) On the wagon. DNA polymerase joins "H-bonds anonymous". *Nature Biotech.* 17, 640-641.]. Indeed, this teaching continues even today [Malyshev et al. (2014) A semi-synthetic organism with an expanded genetic alphabet. *Nature* 509.7500: 385-388] [Zhang et al. (2017) A semisynthetic organism engineered for the stable expansion of the genetic alphabet. *Proc. Natl. Acad. Sci. USA:* 201616443]. Here, an additional pair is taught that lacks inter-strand hydrogen bonding of any kind, but purportedly still fits the rules of size complementarity.

Figure 9:
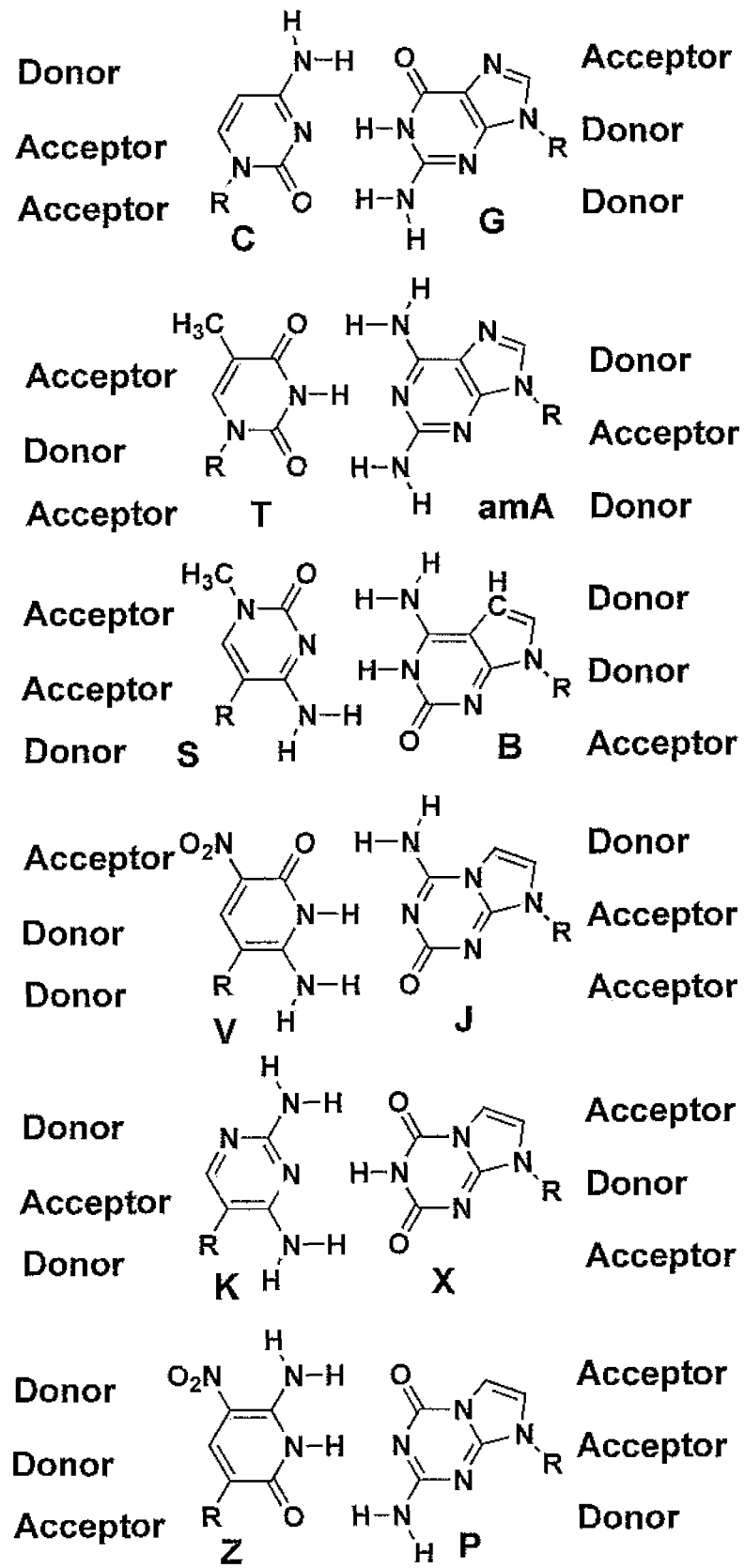

These rules have been generalized to include nucleobases where hydrogen bonding units are swapped. This creates new nucleobase pairs joined by nonstandard patterns of hydrogen bonding. For example, U.S. Pat. No. 5,432,272 disclosed eight additional nucleobases that form four additional pairs by changing the pattern of hydrogen bond donor and acceptor groups presented by a nucleobase to the nucleobase on a complementary oligonucleotide analog. These disclosures showed that the geometry of the Watson-Crick nucleobase pair could accommodate as many as 12 nucleobases forming 6 mutually exclusive pairs (FIG. 9.).

From time to time, reports have appeared in the literature where the Watson-Crick size complementarity has been violated. For example, in 2003, Geyer et al. determine the melting temperatures of a large number of duplexes containing standard and nonstandard pairs [Geyer, C. R., Battersby, T. R., Benner, S. A. (2003) Nucleobase pairing in expanded Watson-Crick like genetic information systems. The nucleobases. *Structure* 11, 1485-1498]. The overwhelming number of these duplexes were formed with pairs that obey the size complementarity rule. However, contained within the ca. 100 duplexes reported were individual cases where a small pyrimidine analog was paired with another small pyrimidine analog, while retaining hydrogen bonding complementarity. Duplexes violating Watson-Crick geometry in this way (small pairing with small) had lower stability, and the investigation was not continued to examine two or more of these "skinny" pairs in a single duplex.

Geyer et al. [op. cit.] also disclosed duplexes where a single large purine analogue was paired with another large purine. Again, the stability of the duplex was generally lower than the stability of duplexes containing fully size complementary pairs, and the investigation was not continued to examine two or more of these "fat" pairs in a single duplex. Further, the pairing was proposed to arise in a geometry where one large purine (or purine analog) case had rotated around the glycosidic bond to present its "Hoogsteen" edge to its pairing partner. This restored, in large part, imperfect size complementarity between the two purines, Fat pairs without this rotation are, however, proposed elsewhere in the art. For example, Seela et al. proposed a "fat" pair between isoguanosine and a functionalized imidazo[1,2-a]-1,3,5-triazine (FIG. 1) [Seela, F., Amberg, S., Melenewski, A. and Rosemeyer, H. (2001) 5-Aza-7-deazaguanine DNA: Recognition and strand orientation of oligonucleotides incorporating anomeric imidazo[1,2-a]-1,3,5-triazine nucleosides. *Helv. Chim. Acta* 84, 1996-2014]. This was an example where the Watson-Crick size complementarity rule is violated, assuming that no rotation occurred. In their model, they assumed that three hydrogen bonds were formed between the purine and the purine analog. Further, they reported molecular recognition between two oligonucleotide strands involving one, two consecutive, or three consecutive pairs.

Figure 2:
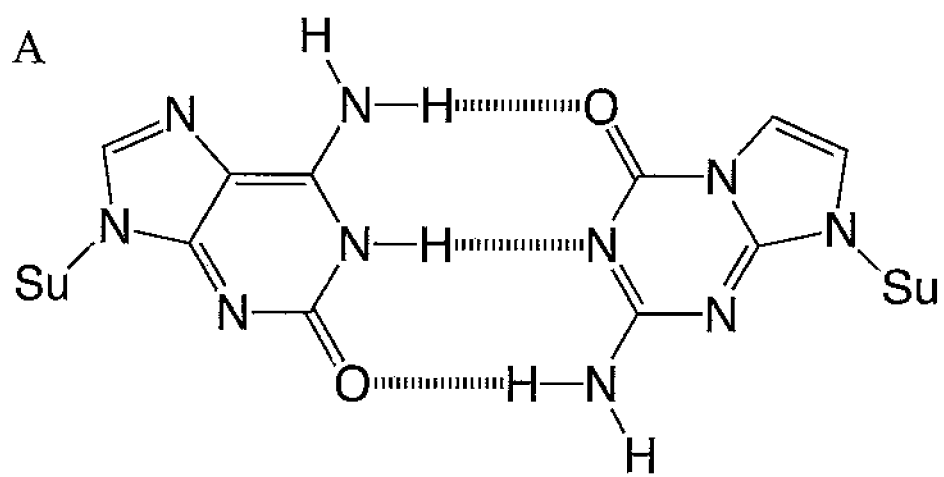
Figure 2:
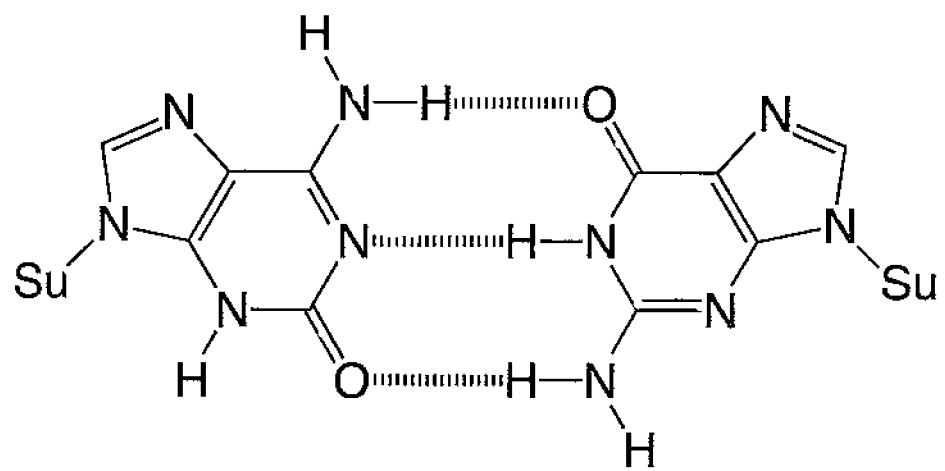

Heuberger and Switzer also reported interaction between the same purine isoguanosine, but pairs to another standard purine, guanine (FIG. 2) [Heuberger, B. D. and Switzer, C. (2008). An alternative nucleobase code: Characterization of purine-purine DNA double helices bearing guanine-isoguanine and diaminopurine 7-deaza-xanthine base pairs. *ChemBioChem*, 9, 2779-2783]. Here, however, a tautomer of isoguanine was proposed, the N3(H) tautomer (FIG. 2). This tautomer of isoguanine is different from the one proposed by Seela in its interaction with the triazine. This suggested that this pairing that violates size commentary rules may not be specific only in the second tautomer was hydrogen bonding complementarity possible.

Isoguanine was also examined as a partner with guanine by Buckley et al. and Kuruvilla et al. [Buckley, R., Enekwa, C. D., Williams L. D. and Hud, N. V. (2011) Molecular recognition of Watson-Crick-like purine-purine base pairs. *ChemBioChem*, 12, 2155-2158] [Kuruvilla, E., Schuster, G. B. and Hud, N. V. (2013) Enhanced nonenzymatic ligation of homopurine miniduplexes: Support for greater base stacking in a Pre-RNA World. *ChemBioChem*, 14, 45-48.]. No biophysical data were presented in these publications. Nevertheless, the art presumes an N3(H) tautomer for isoguanine, because this is the tautomer that can form three inter-pair hydrogen bonds with a guanine partner in a fat, anti-anti, pair.

A few items of art also examine the purine:purine analog pair between diaminopurine and 7-deazaxanthine [Heuberger, B. D. and Switzer, C. (2008) An alternative nucleobase code; Characterization of purine-purine DNA double helices bearing guanine-isoguanine and diaminopurine 7-deaza-xanthine base pairs. *ChemBioChem* 9, 2779-2783] [Kuruvilla, E., Schuster, G. B. and Hud, N. V. (2013) Enhanced nonenzymatic ligation of homopurine miniduplexes: Support for greater base stacking in a pre-RNA World. *ChemBioChem* 14, 45-48.]. The first paper suggested the possibility of an "alternative code", meaning a rule-based molecular recognition system, where isoguanosine (as its N3(H) tautomer) pairs with guanine, and diaminopurine pairs with xanthosine or 7-deazaxanthosine. Here, the longest duplex examined had 12 of these "fat" pairs, with a melting temperature higher (60.3 versus 55.3° C. than a reference pair that obeyed the size complementarity rule.

Finally, a purine:purine pair was examined by Buckley et al., where the "fat" pair was joined by only two hydrogen bonds [Buckley, R., Enekwa, C. D., Williams L. D. and Hud, N. V. (2011) Molecular recognition of Watson-Crick-like purine-purine base pairs. *ChemBioChem*, 12, 2155-2158]. No biophysical data were presented unique to this paper. Nevertheless, the stability of "fat" pairs was attributed to greater stacking energy, possible with the two larger ring systems.

BRIEF SUMMARY OF THE INVENTION

This invention is based on the discovery of an unexpected stability of duplexes that violate the Watson-Crick size complementary pairing rule, but where that violation does involve the pairing of large purines with other purines, but rather where that rule is violated by pairing a small heterocycle with another small heterocycle, a "skinny" pair. Thus, this invention comprises compositions of matter that are one or more oligonucleotides or oligonucleotide analogs that form extended duplex regions where pyrimidine analogs pair with other pyrimidine analogs, at least three consecutively. This pairing does not benefit by greater stacking interactions. However each pair is joined by three hydrogen bonds; and the chains forming the duplexes have an antiparallel orientation.

BRIEF DESCRIPTION OF THE SEVERAL VIEWS OF THE DRAWING(S)

FIG. 1. Isolated cases from the art of "fat" pairs between two purine analogs, including one that donor:acceptor:donor pattern, and the other presenting the hydrogen bonding acceptor:donor:acceptor pattern. Su=sugar of oligonucleotide, the point of attachment of the heterocycle to the oligonucleotide chain.
A. From Shaikh, K. I., Leonard, P. and Seela, F. (2007) 7-Deaza-2'-deoxyxanthosine; nucleobase protection and base pairing of oligonucleotides. *Nucleosides, Nucleotides, and Nucleic Acids*, 26, 737-741.
B. From Kuruvilla, E., Schuster, G. B. and Hud, N. V. (2013) Enhanced nonenzymatic ligation of homopurine miniduplexes: Support for greater base stacking in a pre-RNA world. *ChemBioChem*, 14, 45-48.
C. From: Heuberger, B. D. and Switzer, C. (2008) An alternative nucleobase code; characterization of purine-purine DNA double helices bearing guanine-isoguanine and diaminopurine 7-deaza-xanthine base Pairs. *ChemBioChem*, 9, 2779-2783.
D. From: Buckley, R., Enekwa, C. D., Williams L. D. and Hud, N. V. (2011) Molecular recognition of Watson-Crick-like purine-purine base pairs. *ChemBioChem*, 12, 2155-2158.

FIG. 2. Isolated cases from the art of "fat" pairs between two purine analogs, one that is isoguanine, the other that matches respectively the N1(H) tautomer of isoguanosine, the other that matches the N3(H) tautomer of isoguanosine. Su=sugar of oligonucleotide, the point of attachment of the heterocycle to the oligonucleotide chain.

A. From Seela, F., Amberg, S., Melenewski, A. and Rosemeyer, H. (2001) 5-Aza-7-deazaguanine DNA: Recognition and strand orientation of oligonucleotides incorporating anomeric imidazo[1,2-a]-1,3,5-triazine nucleosides. *Helv. Chim. Acta*, 84, 1996-2014.

B. From: Heuberger, B. D. and Switzer, C. (2008) An Alternative Nucleobase Code: Characterization of Purine-Purine DNA Double Helices Bearing Guanine-Isoguanine and Diaminopurine 7-Deaza-Xanthine Base Pairs. *ChemBioChem*, 9, 2779-2783. Kuruvilla, E., Schuster, G. B. and Hud, N. V. (2013) Enhanced nonenzymatic ligation of homopurine miniduplexes: Support for greater base stacking in a pre-RNA World. *ChemBioChem*, 14, 45-48. Buckley, R., Enekwa, C. D., Williams L. D. and Hud, N. V. (2011) Molecular recognition of Watson-Crick-like purine-purine base pairs, *ChemBioChem*, 12, 2155-2158.

Figure 3:
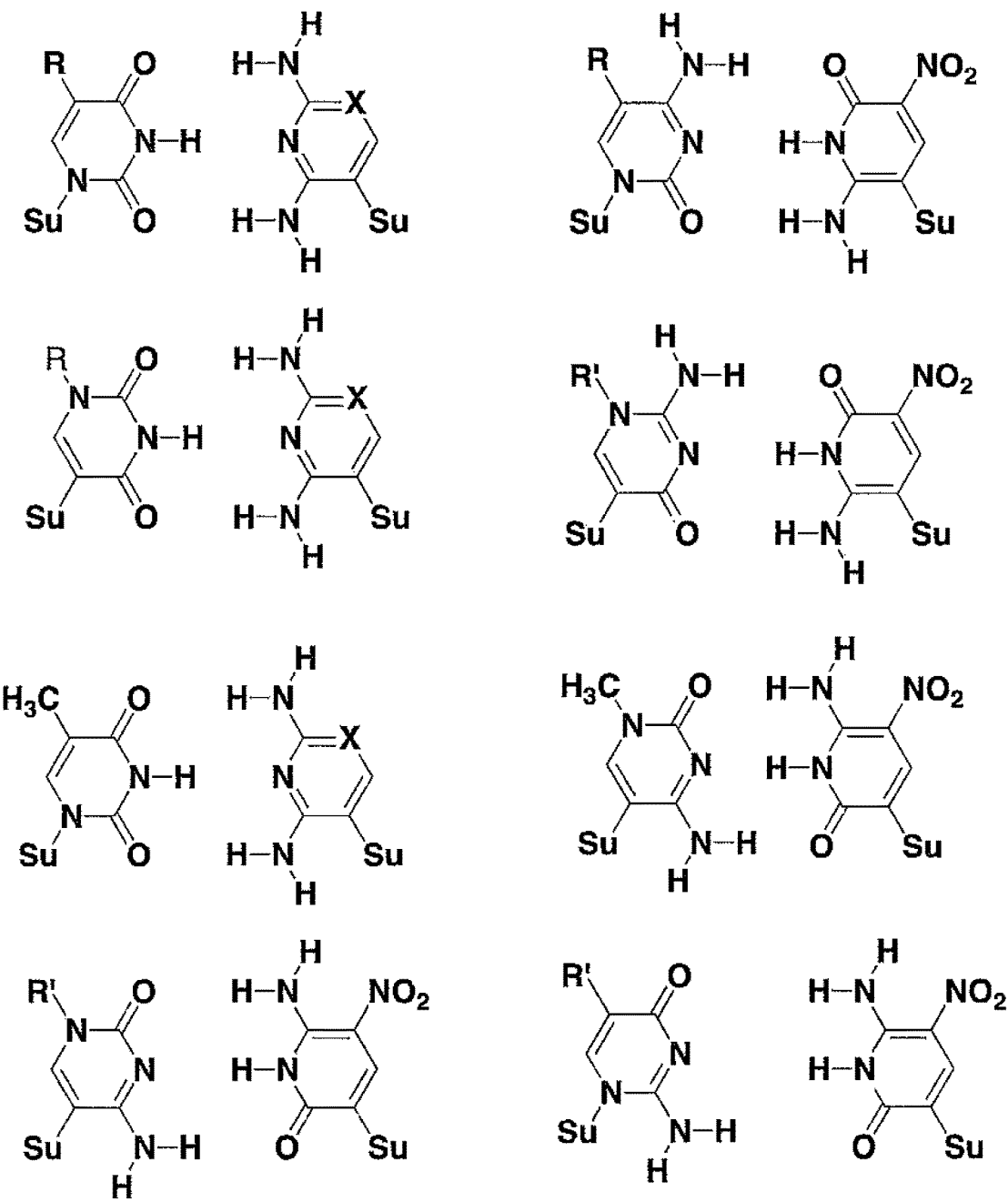

FIG. 3. Skinny pairs of the instant invention. Note that more than one heterocycle can implement the various hydrogen bonding patterns. R'=CH$_3$, alkyl, alkenyl, alkynyl functionalized alkyl, alkenyl, or alkynyl. Su=sugar of oligonucleotide, the point of attachment of the heterocycle to the oligonucleotide chain. R=H, CH$_3$, alkyl, alkenyl, alkynyl functionalized alkyl, alkenyl, or alkynyl. X=N, C—NO$_2$.

Figure 4:
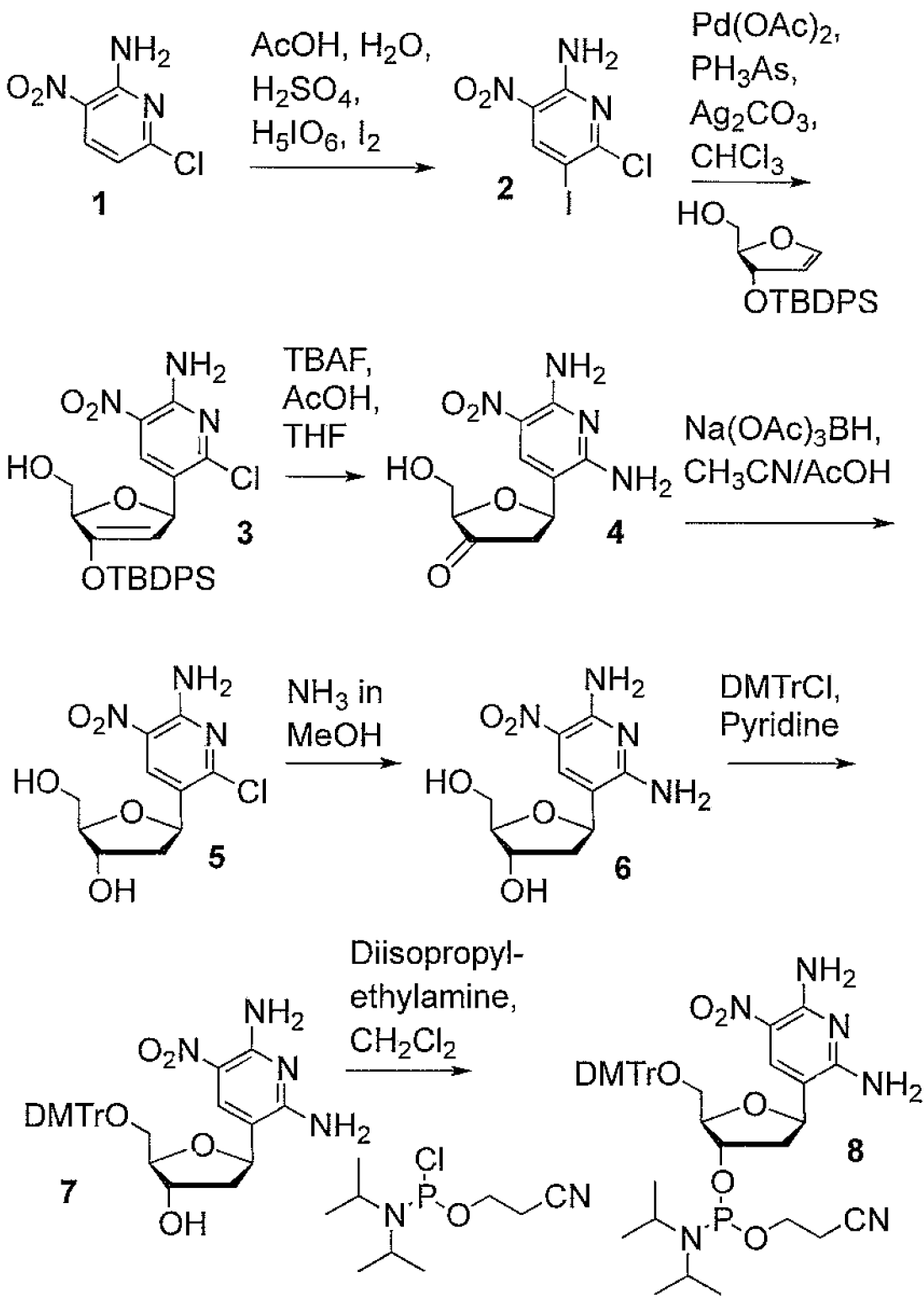

FIG. 4. Synthetic route to make the protected phosphoramidite carrying the small 2,6-diamino-3-nitropyridine, which implements the donor-acceptor-donor K hydrogen bonding pattern.

Figure 5:
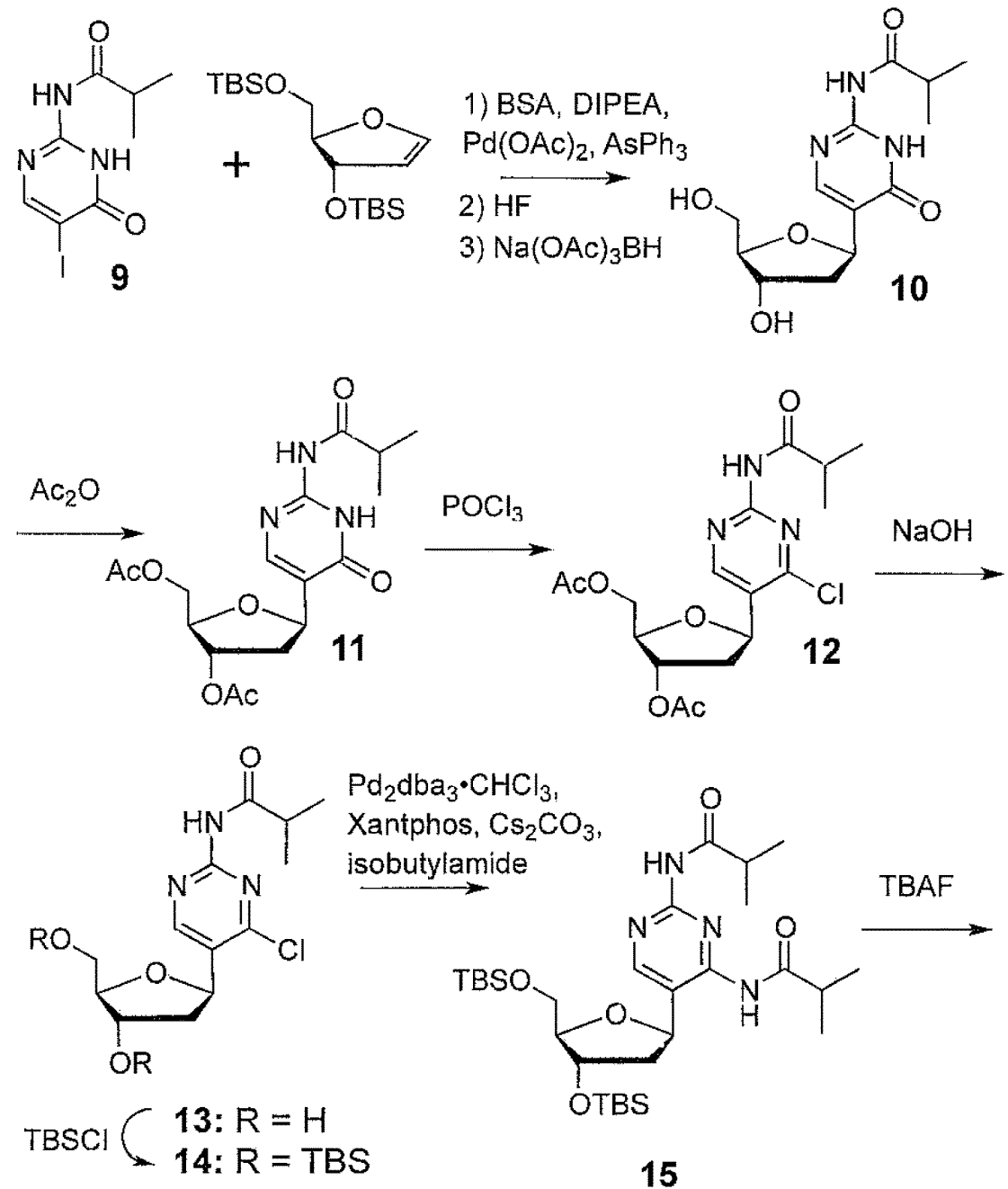

FIG. 5. Synthetic route to make the protected phosphoramidite carrying the small diamino-pyridine, which implements the donor-acceptor-donor K hydrogen bonding pattern. Part 1.

Figure 6:
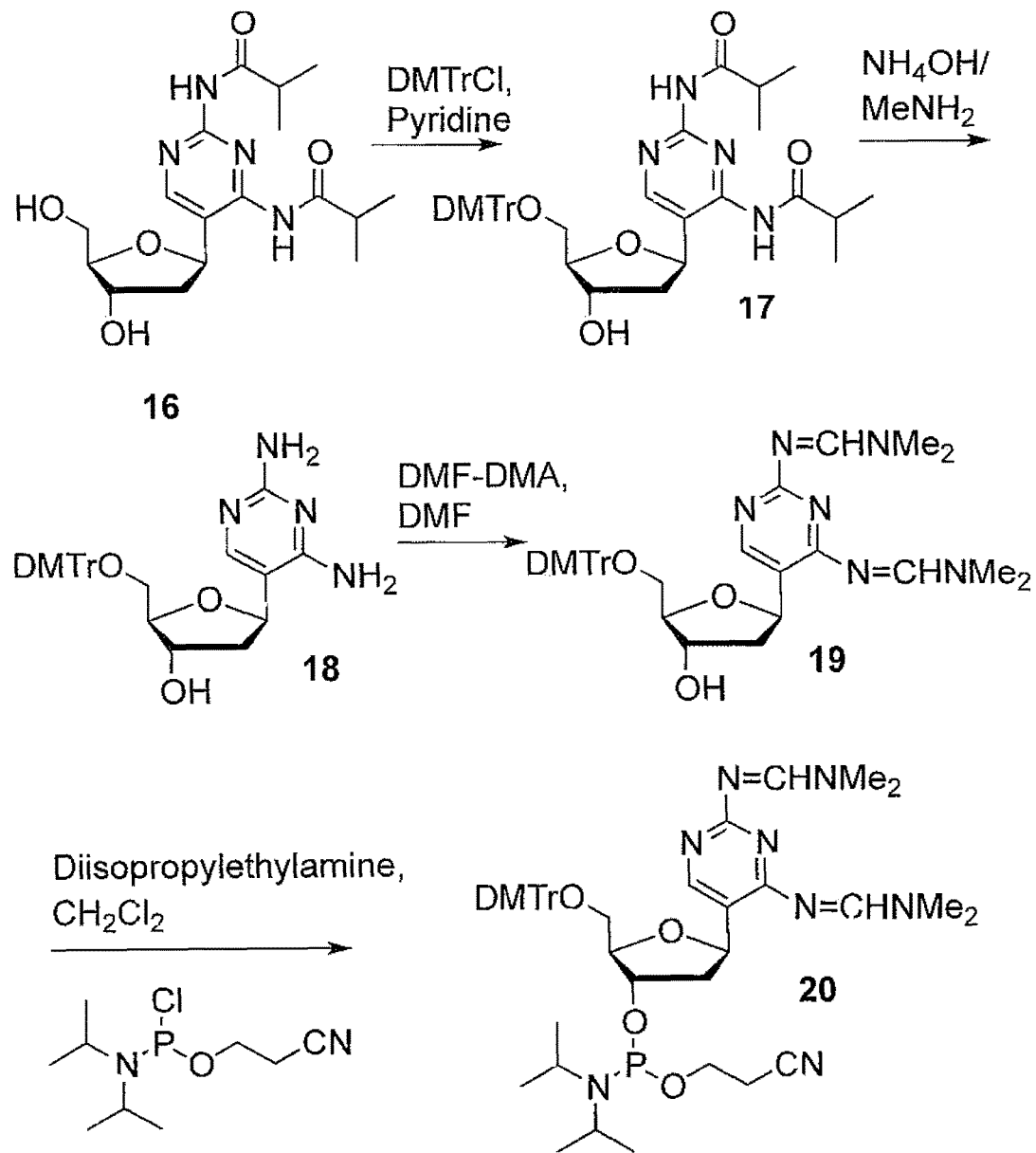

FIG. 6. Synthetic route to make the protected phosphoramidite carrying the small 2,4-diaminopyrimidine, which implements the donor-acceptor-donor K hydrogen bonding pattern. Part 2.

Figure 7:
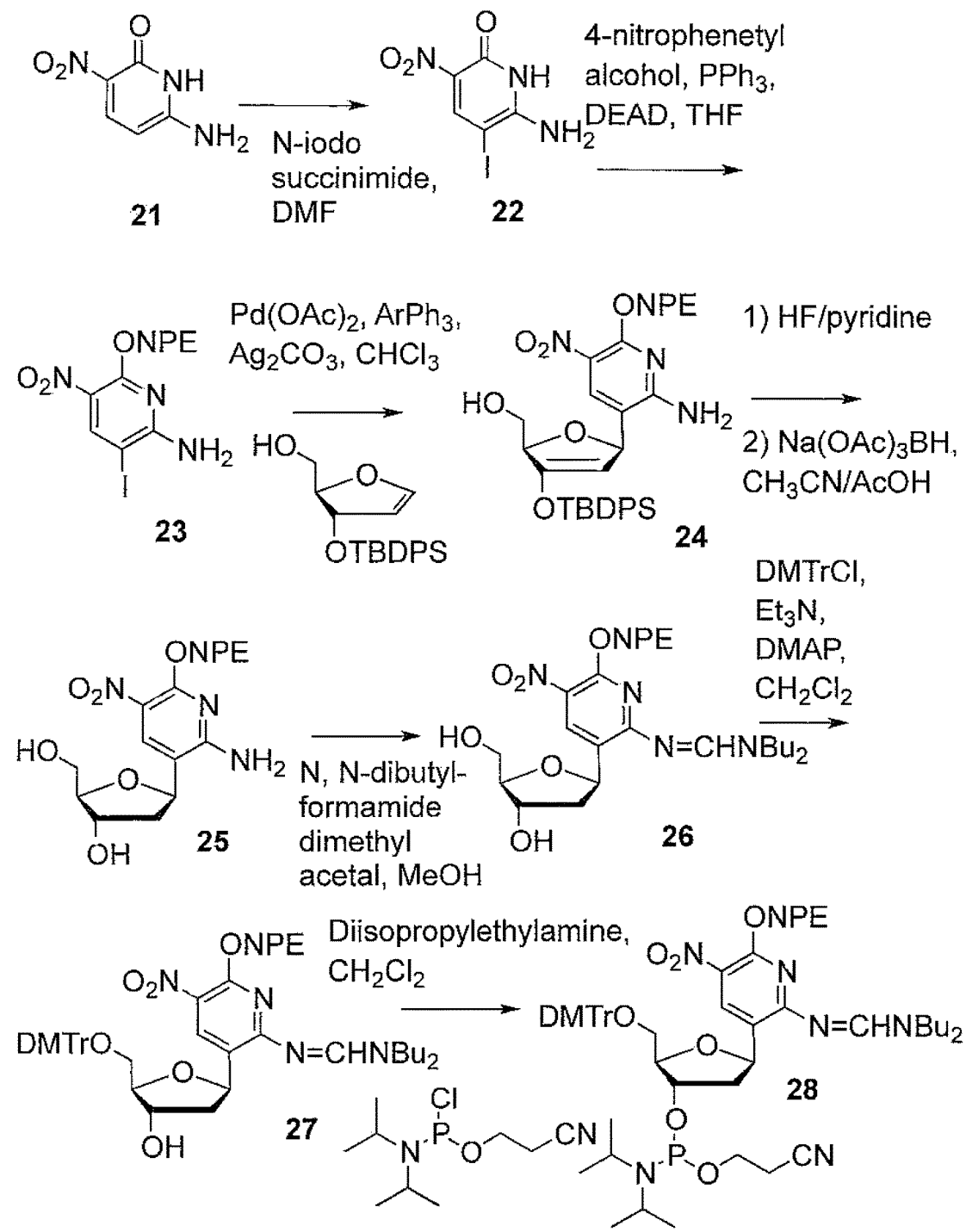

FIG. 7. Synthetic route to make the protected phosphoramidite for the 6-amino-3-nitropyridin-2-one heterocycle, implements the acceptor-donor-donor V hydrogen bonding pattern.

Figure 8:
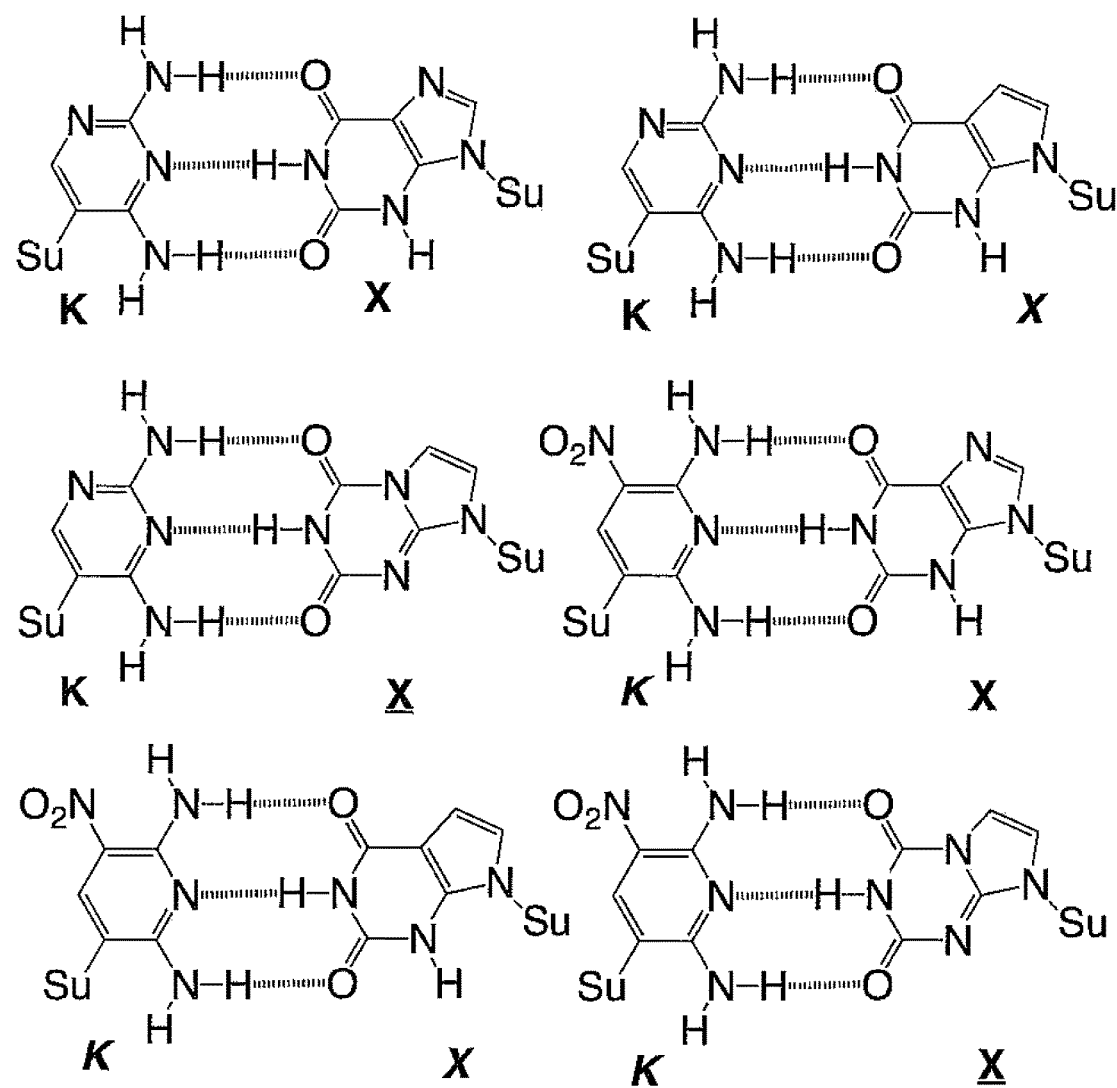

FIG. 8. Some non-standard purines and purine analogs that pair with some of the small pairs disclosed here, but with size complementarity. Note the two implementations of the donor-acceptor-donor K hydrogen bonding pattern. The implementation on 2,4-diaminopyrimidine is unitalicized K; the implementation on 2,6-diamino-3-nitropyridine_is italicized K. In the size complementary Watson-Crick pairing shown here, its partner must present the acceptor-donor-acceptor X hydrogen bonding pattern. This is implemented in three deoxyribonucleosides: xanthosine (unitalicized, not bold X), 7-deazaxanthosine (italicized, not bold X), and 8H-1,3,5-triazine-2(8H)-4(31-H)-dione (unitalicized, bold X). The same nomenclatures is used in the tables reporting reference melting temperatures.

FIG. 9. Structures of other Watson-Crick pairs on nucleobases nucleotides implementing various hydrogen bonding patterns.

DETAILED DESCRIPTION OF THE INVENTION

This invention comprises the formation of duplex structures by the pairing of single strands of DNA/RNA like oligomers, where the heterocycles on each strand are "small" (consist of a single six membered ring attached to a ribose or ribose derivative), and where the heterocycles matched on the two strands in an anti-parallel orientation form three inter-strand hydrogen bonds. Conjecturally, this requires six heterocycles, each having six atoms in the ring, that implement the following hydrogen bonding patterns, written from top to bottom:

Donor-acceptor-donor (DAD): this hydrogen bonding pattern is abbreviated "K".

Donor-donor-acceptor (DDA): this hydrogen bonding pattern is abbreviated "Z".

Acceptor-donor-donor (ADD): this hydrogen bonding pattern is abbreviated "V".

Acceptor-donor-acceptor (ADA): this hydrogen bonding pattern is abbreviated "T".

Acceptor-acceptor-donor (AAD): this hydrogen bonding pattern is abbreviated "S".

Donor-acceptor-acceptor (DAA): this hydrogen bonding pattern is abbreviated "C".

According to the rules of molecular recognition taught in this disclosure, K pairs with T, Z pairs with S, and V pairs with C to form "skinny" pairs.

Another teaching at the instant disclosure is that different heterocyclic systems can implement the same hydrogen bonding pattern. For example, the ADA hydrogen bonding pattern "T" can be implemented on a uracil heterocycle, a thymine heterocycle, or a pseudo-uracil heterocycle, where the heterocycle is attached to the sugar (and the rest of the oligonucleotide chain). Likewise, the donor-acceptor-donor hydrogen bonding pattern K can be implemented by the 2,4-diaminopyrimidine heterocycle or by the 2,6-diamino-3-nitropyridine heterocycle. Synthesis of various of these heterocycles, when not previously known in the art, are given as examples.

Oligonucleotides are synthesized by solid phase DNA synthesis procedures well-known in the art. These syntheses are done using controlled pore glass as a support. Nucleotide building blocks are in the form of protected phosphoramidites, where the phosphorus carries preferably a diisopropylamino group and preferably a beta-cyanoethyloxy group.

The preferred protecting group on the 2,4-diaminopyrimidine heterocycle is N,N-dimethylformamidine. This implements the donor-acceptor-donor K hydrogen bonding pattern. After nucleotide is synthesized, these are removed by treatment with ammonium hydroxide (concentrated, 55° C., approximately 16 hours).

The preferred protecting group on the N1-methyl-4-aminopyrimidin-2-one heterocycle, whose deprotected form implements the acceptor-acceptor-donor S hydrogen bonding pattern, is dialkylformamidine.

The preferred protecting group on 6-amino-5-nitropyridin-2-one heterocycle whose deprotected form implements the acceptor-acceptor-donor Z hydrogen bonding pattern is nitrophenylethyl for the oxygen, and acetyl on the nitrogen.

The preferred protecting group on 6-amino-3-nitropyridin-2-one, whose deprotected form implements the acceptor-acceptor-donor V hydrogen bonding pattern is nitrophenylethyl for the oxygen, and dibutylformamidine on the nitrogen.

The protection of heterocycles implementing the T and C hydrogen bonding patterns, including thymine and cytosine, are well-known in the art.

The compositions of matter covered in the claims are bound species between a first oligonucleotide strand built from building blocks selected from the group K, T, Z, C, V and S, or some subset of these, where the sequence is independently pre-selected. This oligonucleotide is then bound to a second nucleotide also built from these building blocks, but with a sequence selected to be complementary to the first oligonucleotide strand when oriented antiparallel following the rules K pairs with T, Z pairs with S, and V pairs with C.

By "oligonucleotide", it is understood in the instant invention that these include species built from building blocs that comprise a single phosphate moiety, a 2'-deoxyribose moiety, and a heterocycle moiety, where the heterocycle is joined to carbon-1 of the 2'-deoxyribose moiety in the "beta" configuration, and the building blocks are linked via phosphodiester bonds. DNA is the archetypal form of an oligonucleotide, and the "skinny" pairs of the instant invention include the standard DNA pyrimidine nucleotides where the heterocycle is thymine and cytosine. However, in the instant invention, oligonucleotides may also comprise other heterocycles comprising a single ring with six atoms, including uracil, diaminopyrimidine, and others disclosed here. The only requirement is that the heterocycle be able to present three hydrogen bonding groups to a heterocycle that is paired on an antiparallel strand of another oligonucleotide, where the paired heterocycle has a complementary set of three hydrogen bonding groups. Further, the oligonucleotides of the instant invention may comprise other standard nucleobases guanine and adenine (although not in the regions forming skinny nucleobase pairs), as well as many of their analogs, including 7-deazaguanine and diaminopurine.

Further, the instant invention is not limited to compositions that have only two oligonucleotide strands. Three or more oligonucleotides may interact in the claimed compositions. The only limitation is that the inventive parts of these compositions are the segments of those oligonucleotides that interact with other segments via skinny pairs. Further, the instant invention also covers a single oligonucleotide that folds on itself so long as the fold is stabilized by two or more segments within that oligonucleotide that interact with each other via skinny pairs.

Finally, well known in the art are nucleotide building blocks where the nucleobase heterocycle has appended to it a side chain that carries a functional group. For example, thymidine, which has a nucleobase that implements the T acceptor-donor-acceptor hydrogen bonding pattern, is available commercially that has its 5-methyl group replaced by an alkenyl linker or an alkynyl group, to which is appended an aliphatic chain comprising preferably one or two methylene ($CH_2$) units (is possibly more), to which is appended a functional group, preferably an amino group or a thiol group. A represented publication, which is incorporated in its entirety by reference is [Held, H. A., Benner, S. A. (2002) Challenging artificial genetic systems: Thymidine analogs with 5-position sulfur functionality. *Nucl. Acids Res.* 30, 3857-3869.]. A fluorescent tag may be appended to the amino or thiol group.

Likewise, similar tags are well-known in the art as commercial products with similarly derivatized or underivatized side chains appended to the analogous position of cytosine; these are used for sequencing using cyclic reversible termination architectures, the details of which are incorporated by reference. Likewise, various implementations of pyrimidine heterocycles that implement the S acceptor-acceptor-donor hydrogen bonding pattern can have the preferred methyl group at the analogous position replaced by an alkenyl linker or an alkynyl group, derivatized or underivatized.

EXAMPLES

Example 1. Implementation of the Donor-Acceptor-Donor Hydrogen Bonding Pattern on a 2,6-diamino-3-nitropyridine heterocycle (FIG. 4)

Compound 2. A mixture of 2-amino-6-chloro-3-nitropyridine (1, 5.7 g, 32.8 mmol), water (4.5 mL), c-$H_2SO_4$ (1.26 mL) and $H_5IO_6$ (1.59 g) was stirred for 15 min at 95° C. Iodine (3.6 g) was added in portions. The reaction mixture was stirred for 1 h at 95° C., cooled to room temperature, poured into sat. aqueous sodium thiosulfate solution and extracted with ethyl acetate. The organic layer was dried ($Na_2SO_4$), filtered and concentrated. The residue was purified by silica gel column chromatography (Hex/EtOAc=3/2) to give compound 2 (8.7 g, 29.1 mmol, 88%).
$^1$H NMR (DMSO-$d_6$, 300 MHz) δ8.62 (s, 1H), 8.26 (brs, 2H)

Compound 3: A solution of palladium acetate (187 mg, 0.83 mmol) and triphenyl arsine (509 mg, 1.66 mmol) in chloroform (30 mL) was stirred for 30 min at room temperature. This solution was added to the mixture of glycal (3.25 g, 9.2 mmol), 2 (2.49 g, 8.3 mmol) and silver carbonate (4.59 g, 16.6 mmol) in chloroform (60 mL) at room temperature. The reaction mixture was refluxed overnight, cooled to room temperature and filtered through a celite pad, the filtrate was concentrated and the residue was purified by silica gel column chromatography (Hex/EtOAc=4/1 to 7/3) to give compound 3 (2.75 g, 5.23 mmol, 63%) as an orange foam.
$^1$H NMR (CDCl$_3$, 300 MHz) δ8.42 (s, 1H), 7.73-7.82 (m, 4H), 7.41-7.48 (m, 6H), 5.83 (nm, 1H), 7.77 (m, 1H), 4.23 (s, 1H), 3.90 (m, 2H), 1.78 (t, 1H, J=6.0), 1.23 (t, 1H, J=6.9), 1.08 (s, 9H).

Compound 5: To a stirred solution of 3 (2.75 g, 5.23 mmol) in THF (60 mL) as added AcOH (1.5 mL), followed by addition of 1M TBAF in THF (7.9 mL) at 0° C. After 30 min stirring, the reaction mixture was concentrated to give crude compound 4, which was dissolved in $CH_3CN$/AcOH (46 mL/23 mL). To this mixture was added Na(OAc)$_3$BH (1.66 g, 7.83 mmol) at 0° C. After 1 h stirring at 0° C., acetone was added and the reaction mixture was concentrated. The residue was purified by silica gel column chromatography ($CH_2Cl_2$/MeOH=15/1) to give compound 5 (1.21 g, 4.18 mmol, 80%) as a yellow solid.
$^1$H NMR (DMSO-$d_6$, 300 MHz) δ8.49 (s, 1H), 8.14 (brs, 2H), 5.13 (d, 1H, J=3.9), 5.06 (dd, 1H, J=5.7, 9.9), 4.83 (t, 1H, J=5.4), 4.17 (m, 1H), 3.78 (m, 1H), 3.43-3.52 (m, 2H), 2.16 (dd, 1H, J=5.7, 12.6), 1.66 (m, 1H).

Compound 6: Compound 5 (1.2 g, 4.14 mmol) was dissolved in 7 N $NH_3$ in MeOH (80 mL) and heated overnight at 110° C. The reaction mixture cooled and concentrated. The residue was washed with ethanol/ether mixture to give compound 6 (1 g, 3.7 mmol, 90%) as a yellow solid.
$^1$H NMR (DMSO-$d_6$, 300 MHz) δ7.96 (s, 1H), 7.25 (brs, 4H), 5.01-5.15 (m, 2H), 4.88 (dd, 1H, J=6.3, 9.6), 4.20 (m, 1H), 3.74 (m, 1H), 3.47-3.58 (m, 2H), 1.89-1.97 (m, 2H)
$^{13}$C NMR (DMSO-$d_6$, 75 MHz) δ160.6, 155.4, 133.7, 118.2, 112.7, 88.4, 78.1, 72.7, 62.1, 40.9.

Compound 7. To a stirred solution of 6 (310 mg, 1.15 mmole) in pyridine (20 mL) was added DMTCl (428 mg, 1.26 mmole) at room temperature. After being stirred at room temperature for 3 h, catalytic amounts of DMAP were added. The reaction mixture was stirred for additional 1 hour and concentrated. The residue was purified by silica gel column chromatography (Hex/EtOAc=½ to ¼) to give compound 7 (410 mg, 0.72 mmole, 62%).

$^1$H-NMR (300 MHz, DMSO-$d_6$): δ 8.07 (s, 1H), 6.79-8.0 (m, 17H), 5.13 (d, 1H, J=3.9), 4.94 (dd, 1H, J=9.0, 6.0), 4.11 (m, 1H), 3.85 (m, 1H), 3.71 (s, 6H), 3.08 (d, 2H, J=3.6), 2.15 (m, 1H), 1.86 (m, 1H).

Compound 8. To a stirred solution of compound 7 (2.23 g, 3.9 mmole) in $CH_2Cl_2$ (80 mL) were added N,N-diisopropylethylamine (1.02 mL, 5.86 mmole) and 2-cyanoethyl N,N-diisopropylchloro phosphoramidite (1.13 mL, 5.1 mmole) at room temperature. The reaction mixture was stirred at room temperature for 30 min and extracted with water. The organic layer was dried ($Na_2SO_4$), filtered and concentrated. The residue was purified by neutral silica gel column chromatography (Hex/EtOAc=1/4) to give compound 8 (2.62 g, 3.4 mmole, 87%).

$^1$H-NMR (300 MHz, $CDCl_3$): δ 8.10, 8.08 (2s, 1H), 6.80-7.35 (m, 13H), 5.00 (m, 1H), 4.70 (m, 1H), 4.11 (m, 2H), 3.79 (s, 6H), 3.36-3.67 (m, 5H), 2.62 (m, 1H), 2.42-2.56 (m, 2H), 2.05-2.29 (1H), 1.05-1.28 (m, 12H); $^{31}$P-NMR (120 MHz, $CDCl_3$): δ 149.8, 149.3.

Example 2. Implementation of the Donor-Acceptor-Donor Hydrogen Bonding Pattern on a 2,4-diaminopyrimidine heterocycle (FIG. 5 and FIG. 6)

To synthesized protected K nucleoside, iodo-isocytosine derivative (9) was coupled with glycal and the resulting product was treated with HF/pyridine to give ketone, which was reduced with $NaBH(OAc)_3$ to give compound 10. The two free hydroxyl groups were protected with $Ac_2O$ to give compound 11, which was treated with $POCl_3$ to give compound 12. Before displacing the chloride, the acetyls were replaced by TBS protecting groups by treating with NaOH to give 13, and reacting with TBDMS chloride to give the bis-silyl ether 14. Pd-catalyzed coupling reaction of 14 with the amide of isobutyric acid gave compound 15.

Moving on to FIG. 6, the TBDMS groups were removed using TBAF to give protected dK nucleoside 16. Following protection of the 5'-OH group as the DMT groups in 17, the protecting groups were exchanged to give dK phosphoramidite protected with N,N-dimethylformamidine groups. (FIG. 6). Isobutyroyl groups were removed from 17 by treatment with $NH_4OH/CH_3NH_2$ (1/1) to give the diamine 18. Protection of exocyclic diamino groups of 18 with N,N-dimethylformamide dimethyl acetal gave compound 19. Using standard conditions, 19 was converted to the corresponding phosphoramidite 20.

To determine whether this phosphoramidite 20 can be used for synthesis of oligonucleotide containing dK and dX, dK-dT dimer was synthesized using standard conditions, treated with the following conditions to remove the exocylic amine protection group and analyzed by reverse HPLC. From HPLC analysis, 6% (condition a) and 15% (condition e) of mono protected are still remained, but most Dmf protection groups of dK can be removed under all these conditions.

Example 3. Synthesis of 2'-deoxynucleoside with Heterocycle Implementing the V Hydrogen Bonding Pattern. (FIG. 7)

Compound 22 (6-Amino-5-iodo-3-nitro-2(1H)-pyridone). A mixture of compound 21 (5.0 g, 32.2 mmol) and N-iodosuccinimide (8.7 g, 38.6 mmol) in DMF (100 mL) was stirred at rt for 1 h. The mixture was poured into water (150 mL) and the precipitate was filtered and washed with methanol and dried to give 22 as a yellow solid (3.0 g, 33%). $^1$H NMR (300 MHz, DMSO-$d_6$) δ 8.51 (s, 1H), 7.4~7.6 (br s, 2H).

Compound 23 (3-Iodo-5-nitro-6-[2-(4-nitrophenyl) ethoxy]-2-pyridinamine)

To a mixture of compound 22 (3.0 g, 10.7 mmol), 4-nitrophenethyl alcohol (2.68 g, 16.0 mmol) and triphenylphosphine (4.20 g, 16 mmol) in anhydrous THF (100 mL) was added diethylazodicarboxylate (2.5 mL, 16 mmol). The mixture was stirred at rt for 2 days and evaporated with silica gel. The residue was purified by flash chromatography (silica, hexanes: $CH_2Cl_2$=1:3) to give a yellow solid. It was dispersed in ethyl acetate/hexanes (20 mL/60 mL) and filtered and dried to give compound 23 (2.2 g, 48%). $^1$H NMR (300 MHz, $CDCl_3$) δ 8.59 (s, 1H), 8.17 (d, 2H, J=8.7 Hz), 7.52 (d, 2H, J=8.7 Hz), 5.47 (br s, 2H), 4.57 (t, 2H, J=6.3 Hz), 3.22 (t, 2H, J=6.3 Hz). HRMS (ESI) m/z calculated for $C_{13}H_{11}N_4O_5Na$ (M+Na)$^+$ 452.9672. found 452.9666, m/z calculated for $C_{13}H_{11}IN_4O_5K$ (M+K)$^+$ 468.9411, found 468.9406.

Compound 25 (3-(2'-Deoxy-□eta-D-ribofuranosyl)-5-nitro-6-[2-(4-nitrophenyl)ethoxy]-2-pyridinamine). Palladium acetate (132 mg, 0.6 mmol) and triphenylarsine (366 mg, 1.2 mmol) were dissolved in chloroform (20 mL), and the mixture was stirred at rt for 30 min. Then it was added to a mixture of compound 3 (2.58 g, 6.0 mmol), glycal (2.34 g, 6.6 mmol) and silver carbonate (3.31 g, 12.0 mmol) in chloroform (40 mL). The resulting mixture was refluxed overnight. After cooling to rt, it was filtered through Celite and washed with ethyl acetate. The combined filtrate was concentrated in vacuo. The residue was purified by flash chromatography (silica, ethyl acetate:hexanes=1:1) to give a brown solid (24).

This material, without further characterization, was dissolved in THF (50 mL) and treated with pyridine hydrofluoride (0.5 mL) and stirred at rt for 1 h. The mixture was evaporated with silica gel and the residue was purified by flash chromatography (silica, ethyl acetate) to give a yellow solid. This material was dissolved in acetic acid (20 mL) and acetonitrile (20 mL) and treated with sodium triacetoxyborohydride (1.48 g, 7.0 mmol) and stirred at rt for 2 h. The mixture was poured into brine (150 mL) and extracted with ethyl acetate. The combined organic layers were dried over $Na_2SO_4$, filtered and concentrated. The residue (25) was purified by flash chromatography (silica, ethyl acetate: MeOH=30:1) to give a yellow solid (800 mg, 32% for 3 steps). $^1$H NMR (300 MHz, $CD_3OD$) δ 8.14 (s, 1H), 8.13 (d, 2H, J=9.0 Hz), 7.59 (d, 2H, J=9.0 Hz), 5.02 (dd, 1H, J=11.1, 5.4 Hz), 4.63 (t, 2H, J=6.3 Hz), 4.37 (m, 1H), 3.92 (dd, 1H, J=5.7, 3.0 Hz), 3.72 (d, 2H, J=3.0 Hz), 3.20 (t, 2H, J=6.5 Hz), 2.22 (ddd, 1H, J=13.2, 11.4, 6.3 Hz), 2.00 (ddd, 1H, J=12.9, 7.2, 1.5 Hz).

Compound 26 (N-[(Dibutylamino)methylene]-3-(2'-deoxy-□eta-D-ribofuranosyl)-5-nitro-6-[2-(4-nitrophenyl) ethoxy]-2-pyridinamine) A mixture of compound 25 (1.15 g, 2.74 mmol), and N,N-dibutylformamide dimethyl acetal (1.5 mL) in methanol (20 mL) was stirred at rt overnight. The mixture was evaporated and purified by flash chromatography (neutral silica, ethyl acetate:hexanes=2:1). The major fraction was collected and evaporated to give a compound 26 as a yellow solid (1.08 g, 70%). $^1$H NMR (300 MHz, $CDCl_3$) δ 8.51 (s, 1H), 8.38 (s, 1H), 8.14 (d, 2H, J=9.0 Hz), 7.53 (d, 2H, J=9.0 Hz), 5.40 (dd, 1H, J=9.3, 6.0 Hz), 4.62 (t, 2H, J=6.2 Hz), 4.38 (m, 1H), 3.96 (dd, 1H, J=8.4, 4.5 Hz), 3.75~3.9 (m, 2H), 3.53 (t, 2H, J=7.5 Hz), 3.36 (t, 2H, J=7.2 Hz), 3.23 (t, 2H, J=6.2 Hz), 2.40 (ddd, 1H, J=13.2, 6.0, 2.7 Hz), 1.8~1.9 (m, 1H), 1.55~1.7 (m, 4H), 1.3~1.4 (m, 4H), 0.96 (t, 3H, J=7.2 Hz), 0.95 (t, 3H, J=7.2 Hz). $^{13}$C NMR (75 MHz, CDCl$_3$) δ 160.42, 156.21, 155.48, 147.06, 146.65, 134.11, 130.44, 126.97, 123.83, 123.49, 86.95, 75.61, 73.86, 66.66, 63.61, 52.52, 46.36, 42.94, 35.54, 31.19, 29.40, 20.53, 19.91, 14.11, 13.86.

Compound 27 (N-[(Dibutylamino)methylene]-3-(2'-deoxy-5'-O-dimethoxytrityl-□eta-D-ribofuranosyl)-5-nitro-6-[2-(4-nitrophenyl)ethoxy]-2-pyridinamine)

A mixture of compound 26 (1.08 g, 1.93 mmol), dimethoxytrityl chloride (687 mg, 2.03 mmol), triethylamine (0.54 mL) and DMAP (5 mg) in dichloromethane (50 mL) was stirred at rt for 3 h. It was poured into water and extracted with dichloromethane. The combined organic layer was dried (Na$_2$SO$_4$), filtered and evaporated. The residue was purified by flash chromatography (neutral silica, ethyl acetate hexanes=1:2) to give a compound 17 as a yellow solid (1.50 g, 90%). $^1$H NMR (300 MHz, CDCl$_3$) δ 8.51 (s, 1H), 8.42 (s, 1H), 8.16 (d, 2H, J=8.7 Hz), 7.54 (d, 2H, J=9.0 Hz), 7.2~7.9 (m, 9H), 6.84 (dd, 4H, J=9.0, 1.2 Hz), 5.39 (dd, 1H, J=9.3, 6.0 Hz), 4.62 (t, 2H, J=6.3 Hz), 4.30 (m, 1H), 4.02 (m, 1H), 3.79 (s, 6H), 3.2~3.6 (m, 8H), 2.42 (ddd, 1H, J=12.9, 5.7, 2.4 Hz), 1.55~1.9 (m, 6H), 1.3~1.4 (m, 4H), 0.96 (t, 3H, J=7.2 Hz), 0.95 (t, 3H, J=7.2 Hz). $^{13}$C NMR (75 MHz, CDCl$_3$) δ 159.99, 158.71, 155.91, 155.31, 147.04, 146.66, 145.02, 136.11, 136.01, 133.90, 130.43, 130.29, 128.31, 128.08, 127.15, 127.02, 124.13, 123.81, 113.38, 86.51, 85.70, 75.33, 74.90, 66.58, 64.74, 55.44, 52.45, 46.33, 42.50, 35.54, 31.20, 29.38, 20.54, 19.90, 14.10, 13.85.

Example 4. Synthesis of Oligonucleotides

Support-bound oligonucleotides were synthesized on an Applied BioSystems 394 DNA synthesizer using the following phosphoramidite building blocks (P, Z, S, K, K and X phosphoramidites from Firebird Biomolecular Sciences), (2: 2-Aminopurine-CE Phosphoramidite, D: Pac-2-Amino-dA-CE Phosphoramidite, B: dmf-isodG-CE Phosphoramidite, X: dX-CE Phosphoramidite, X: 7-deaza-dX-CE Phosphoramidite, t: 2-Thio-dT-CE Phosphoramidite and standard Ultramild CE phosphoramidites from Glen Research) and Ultramild CPG supports (Glen Research) at a 1.0 µmol scale following the standard procedure. Each phosphoramidite unit was used at a concentration of 0.1 M in dry CH$_3$CN; coupling times were 10 min for each step. After completion of the synthesis, 1) The CPG support with oligonucleotides with X or Z was treated with 1.0 M DBU in dry CH$_3$CN (2.0 mL) for 24 hours. Then the CPG was washed with CH$_3$CN and dried. The dried CPG was treated with NH$_4$OH (1.0 mL) for 16 h at 55° C.; support was removed by filtration.

2) The CPG support having oligonucleotides containing 2-thioT or X was treated with NH$_4$OH (1.0 mL) for 16 hours at room temperature, and the support was removed by filtration.

3) The CPG support having oligonucleotides containing the other nucleobases was treated with NH$_4$OH (1.0 mL) for 16 hours at 55° C., and the support was removed by filtration.

The filtrate was lyophilized and the residue was purified on ion-exchange HPLC.

Example 5. Measurement of Melting Temperature

Melting temperatures (T$_m$) were measured in a reaction containing 2.0 µM of each oligonucleotide dissolved in buffer (10 mM NaCl, 10 mM sodium cacodylate, pH 6.8). Absorbance was monitored on a Shimadzu UV-Vis Spectrophotometer at 260 nm over a temperature range of 20.0° C. to 90.0° C. with a change in temperature of 0.5° C. per min. The T$_m$ values were determined by averaging the temperatures of the three heating measurements.

To demonstrate the surprising and unexpected pairing potential between two oligonucleotides with the pairs are skinny, the series of melting temperatures were run. Each experiment was run in 10 mM Na cacodylate buffer (pH 6.8) containing 10 mM NaCl. Each oligonucleotide was present at 2 µM concentrations. These studies were done using a systematically varied set of reference 15mers.

Example 5.1: Watson-Crick Base Size Complementary Reference Pairing

The initial experiments are reference experiments that show the melting temperatures of the reference 15mer duplex where size complementarity rules are followed as well as hydrogen bonding complementarity rules. The acceptor-donor-acceptor hydrogen bonding pattern on the large component of the pair was implemented on 7-deazaxanthine. The donor-acceptor-donor hydrogen bonding pattern on the small component was implemented by 2,6-diamino-3-nitropyridine. The acceptor-acceptor-donor hydrogen bonding pattern on the small component is implemented by methylpseudocytidine. The bond donor-donor-acceptor hydrogen bonding pattern implemented on the large complement is implemented by isoguanine. The structures for the other pairs are shown in FIG. 9. Data are in Table 1.

TABLE 1

| Watson-Crick reference pairs. | | |
|---|---|---|
| 5'-CGTCGCCCCCGGCTC-3' | SEQ ID 1 | 56.3 |
| 3'-GCAGCGGGGGCCGAG-5' | SEQ ID 2 | In both of these sequences, only standard nucleotides are present. |
| 5'-CGTCGTTTTTGGCTC-3' | SEQ ID 3 | 48.3 |
| 3'-GCAGCAAAAACCGAG-5' | SEQ ID 4 | In both of these sequences, only standard nucleotides are present. |
| 5'-CGTCGTTPTTGGCTC-3' | SEQ ID 5 | 52.0 |
| 3'-GCAGCAAZAACCGAG-5' | SEQ ID 6 | The letter "P" represents 7-amino-9-(1'-beta-D-2'-deoxyribofuranosyl)-imidazo[1,2-c]pyrimidin-5(1H)-one; the letter "Z" represents 6-amino-3-(2'-deoxy-D-ribofuranosyl)-5-nitro-1H-pyridin-2-one. |
| 5'-CGTCGTPPPTGGCTC-3' | SEQ ID 7 | 63.7 |
| 3'-GCAGCAZZZACCGAG-5' | SEQ ID 8 | The letter "P" represents 7-amino-9-(1'-beta-D-2'-deoxyribofuranosyl)-imidazo[1,2-c]pyrimidin-5(1H)-one; the letter "Z" represents 6-amino-3-(2'-deoxy-D-ribofuranosyl)-5-nitro-1H-pyridin-2-one. |
| 5'-CGTCGPTPTPGGCTC-3' | SEQ ID 9 | 63.3 |

TABLE 1-continued

Watson-Crick reference pairs.

| | | |
|---|---|---|
| 3'-GCAGCZAZAZCCGAG-5' | SEQ ID 10 | The letter "P" represents 7-amino-9-(1'-beta-D-2'-deoxyribofuranosyl)-imidazo[1,2-c]pyrimidin-5(1H)-one; the letter "Z" represents 6-amino-3-(2'-deoxy-D-ribofuranosyl)-5-nitro-1H-pyridin-2-one. |
| 5'-CGTCGPPPPPGGCTC-3' | SEQ ID 11 | 75.7 |
| 3'-GCAGCZZZZZCCGAG-5' | SEQ ID 12 | The letter "P" represents 7-amino-9-(1'-beta-D-2'-deoxyribofuranosyl)-imidazo[1,2-c]pyrimidin-5(1H)-one; the letter "Z" represents 6-amino-3-(2'-deoxy-D-ribofuranosyl)-5-nitro-1H-pyridin-2-one. |
| 5'-CGTCGTTSTTGGCTC-3' | SEQ ID 13 | 49.8 |
| 3'-GCAGCAABAACCGAG-5' | SEQ ID 14 | The letter "S" represents 4-amino-N$^1$-methyl-5-(1'-beta-D-2'-deoxyribofuranosyl)-2(1H)-pyrimidinone; the letter "B" represents 4-amino-3-hydro-7-(2-deoxy-β-D-ribofuranosyl)-pyrrolo[2,3-d]pyrimidin-2-one. |
| 5'-CGTCGTSSSTGGCTC-3' | SEQ ID 15 | 54.9 |
| 3'-GCAGCABBBACCGAG-5' | SEQ ID 16 | The letter "S" represents 4-amino-N$^1$-methyl-5-(1'-beta-D-2'-deoxyribofuranosyl)-2(1H)-pyrimidinone; the letter "B" represents 4-amino-3-hydro-7-(2-deoxy-β-D-ribofuranosyl)-pyrrolo[2,3-d]pyrimidin-2-one. |
| 5'-CGTCGSTSTSGGCTC-3' | SEQ ID 17 | 55.7 |
| 3'-GCAGCBABABCCGAG-5' | SEQ ID 18 | The letter "S" represents 4-amino-N$^1$-methyl-5-(1'-beta-D-2'-deoxyribefuranosyl)-2(1H)-pyrimidinone; the letter "B" represents 4-amino-3-hydro-7-(2-deoxy-β-D-ribofuranosyl)-pyrrolo[2,3-d]pyrimidin-2-one. |
| 5'-CGTCGSSSSSGGCTC-3' | SEQ ID 19 | 61.0 |
| 3'-GCAGCBBBBBCCGAG-5' | SEQ ID 20 | The letter "S" represents 4-amino-N$^1$-methyl-5-(1'-beta-D-2'-deoxyribofuranosyl)-2(1H)-pyrimidinone; the letter "B" represents 4-amino-3-hydro-7-(2-deoxy-β-D-ribofuranosyl)-pyrrolo[2,3-d]pyrimidin-2-one. |
| 5'-CGTCGTT*X*TTGGCTC-3' | SEQ ID 21 | 49.1 |
| 3'-GCAGCAA*K*AACCGAG-5' | SEQ ID 22 | The letter "*K*" represents 2,6-diamino-3-nitro-5-(1'-beta-D-2'-deoxyribofuranosyl)-pyridine; the letter "*X*" represents 2'-deoxy-7-deazaxanthosine. |
| 5'-CGTCGT*XXX*TGGCTC-3' | SEQ ID 23 | 56.0 |
| 3'-GCAGCA*KKK*ACCGAG-5' | SEQ ID 24 | The letter "*K*" represents 2,6-diamino-3-nitro-5-(1'-beta-D-2'-deoxyribofuranosyl)-pyridine; the letter "*X*" represents 2'-deoxy-7-deazaxanthosine. |
| 5'-CGTCG*XTXTX*GGCTC-3' | SEQ ID 25 | 53.1 |
| 3'-GCAGC*KAKAK*CCGAG-5' | SEQ ID 26 | The letter "*K*" represents 2,6-diamino-3-nitro-5-(1'-beta-D-2'-deoxyribofuranosyl)-pyridine; the letter "*X*" represents 2'-deoxy-7-deazaxanthosine. |
| 5'-CGTCG*XXXXX*GGCTC-3' | SEQ ID 27 | 57.9 |
| 3'-GCAGC*KKKKK*CCGAG-5' | SEQ ID 28 | The letter "*K*" represents 2,6-diamino-3-nitro-5-(1'-beta-D-2'-deoxyribofuranosyl)-pyridine; the letter "*X*" represents 2'-deoxy-7-deazaxanthosine. |

TABLE 2

Watson-Crick reference pairs to compare different implementations of the K and X hydrogen bonding patterns.

| | | |
|---|---|---|
| 5'-CGTCGTTXTTGGCTC-3' | SEQ ID 29 | 45.7 |
| 3'-GCAGCAAKAACCGAG-5' | SEQ ID 30 | The letter "K" represents 2,4-diamino-5-(1'-beta-D-2'-deoxyribofuranosyl)-pyrimidine; the letter "X" represents 8-(beta-D-2'-deoxyribofuranosyl)imidazo[1,2-a]-1,3,5-triazine-2(8H)-4(3H)-dione. |
| 5'-CGTCGTTXTTGGCTC-3' | SEQ ID 31 | 48.6 |
| 3'-GCAGCAAKAACCGAG-5' | SEQ ID 30 | The letter "K" represents 2,4-diamino-5-(1'-beta-D-2'-deoxyribofuranosyl)-pyrimidine; the letter "X" represents 2'-deoxyxanthosine. |
| 5'-CGTCGTT*X*TTGGCTC-3' | SEQ ID 21 | 50.5 |
| 3'-GCAGCAA*K*AACCGAG-5' | SEQ ID 30 | The letter "K" represents 2,4-diamino-5-(1'-beta-D-2'-deoxyribofuranosyl)-pyrimidine; the letter "*X*" represents 2'-deoxy-7-deoxyxanthosine. |
| 5'-CGTCGTTXTTGGCTC-3' | SEQ ID 29 | 42.0 |
| 3'-GCAGCAA*K*AACCGAG-5' | SEQ ID 22 | The letter "*K*" represents 2,6-diamino-3-nitro-5-(1'-beta-D-2'-deoxyribofuranosyl)-pyridine; the letter "*X*" represents 8-(beta-D-2'-deoxyribofuranosyl)imidazo[1,2-a]-1,3,5-triazine-2(8H)-4(3H)-dione. |
| 5'-CGTCGTTXTTGGCTC-3' | SEQ ID 31 | 45.3 |
| 3'-GCAGCAA*K*AACCGAG-5' | SEQ ID 22 | The letter "*K*" represents 2,6-diamino-3-nitro-5-(1'-beta-D-2'-deoxyribofuranosyl)-pyridine; the letter "*X*" represents 2'-deoxyxanthosine. |
| 5'-CGTCGTT*X*TTGGCTC-3' | SEQ ID 21 | 49.1 |
| 3'-GCAGCAA*K*AACCGAG-5' | SEQ ID 22 | The letter "*K*" represents 2,6-diamino-3-nitro-5-(1'-beta-D-2'-deoxyribofuranosyl)-pyridine; the letter "X" represents 2'-deoxy-7-deazaxanthosine. |
| 5'-CGTCGTXXXTGGCTC-3' | SEQ ID 32 | 37.1 |
| 3'-GCAGCAKKKACCGAG-5' | SEQ ID 33 | The letter "K" represents 2,4-diamino-5-(1'-beta-D-2'-deoxyribofuranosyl)-pyrimidine; the letter "X" represents 8-(beta-D-2'-deoxyribofuranosyl)imidazo[1,2-a]-1,3,5-triazine-2(8H)-4(3H)-dione. |
| 5'-CGTCGTXXXTGGCTC-3' | SEQ ID 34 | 50.7 |
| 3'-GCAGCAKKKACCGAG-5' | SEQ ID 33 | The letter "K" represents 2,4-diamino-5-(1'-beta-D-2'-deoxyribofuranosyl)-pyrimidine; the letter "X" represents 2'-deoxyxanthosine. |
| 5'-CGTCGT*XXX*TGGCTC-3' | SEQ ID 23 | 55.6 |
| 3'-GCAGCA*KKK*ACCGAG-5' | SEQ ID 33 | The letter "K" represents 2,4-diamino-5-(1'- |

TABLE 2-continued

Watson-Crick reference pairs to compare different implementations of the K and X hydrogen bonding patterns.

beta-D-2'-deoxyribofuranosyl)-pyrimdine; the letter "*X*" represents 2'-deoxy-7-deazaxanthosine.
5'-CGTCGTXXXTGGCTC-3'       SEQ ID 32    39.8
3'-GCAGCA*KKK*ACCGAG-5'    SEQ ID 24    The letter "*K*" represents 2,6-diarnino-3-nitro-5-(1'-beta-D-2'-deoxyribofuranosyl)-pyridine; the letter "X" represents 8-(beta-D-2'-deoxyribofuranosyl)imidazo[1,2-a]-1,3,5-triazine-2(8H)-4(3H)-dione.
5'-CGTCGTXXXTGGCTC-3'        SEQ ID 34    46.7
3'-GCAGCA*KKK*ACCGAG-5'    SEQ ID 24    The letter "*K*" represents 2,6-diarnino-3-nitro-5-(1'-beta-D-2'-deoxyribofuranosyl)-pyridine; the letter "X" represents 2'-deoxyxanthosine.
5'-CGTCGT*XXX*TGGCTC-3'      SEQ ID 23    56.0
3'-GCAGCA*KKK*ACCGAG-5'    SEQ ID 24    The letter "*K*" represents 2,6-diarnino-3-nitro-5-(1'-beta-D-2'-deoxyribofuranosyl)-pyridine; the letter "*X*" represents 2'-deoxy-7-deazaxanthosine.
5'-CGTCGXTXTXGGCTC-3'    SEQ ID 35    44.2
3'-GCAGCKAKAKCCGAG-5'        SEQ ID 36    The letter "K" represents 2,4-diamino-5-(1'-beta-D-2'-deoxyribofuranosyl)-pyrimidine; the letter "X" represents 8-(beta-D-2'-deoxyribofuranosyl)imidazo[1,2-a]-1,3,5-triazine-2(8H)-4(3H)-dione.
5'CGTCGXTXTXGGCTC-3'         SEQ ID 37    50.0
3'-GCAGCKAKAKCCGAG-5'        SEQ ID 36    The letter "K" represents 2,4-diamino-5-(1'-beta-D-2'-deoxyribofuranosyl)-pyrimidine; the letter "X" represents 2'-deoxyxanthosine.
5'-CGTCG*XTXTX*GGCTC-3'      SEQ ID 25    57.7
3'-GCAGCKAKAKCCGAG-5'        SEQ ID 36    The letter "K" represents 2,4-diamino-5-(1'-beta-D-2'-deoxyribofuranosyl)-pyrimidine; the letter "*X*" represents 2'-deoxy-7-deazaxanthosine.
5'-CGTCGXTXTXGGCTC-3'    SEQ ID 35    41.9
3'-GCAGC*KAKAK*CCGAG-5'      SEQ ID 26    The letter "*K*" represents 2,6-diarnino-3-nitro-5-(1'-beta-D-2'-deoxyrihofuranosyl)-pyridine; the letter "X" represents 8-(β-D-2'-deoxyribofuranosyl)imidazo[1,2-a]-1,3,5-triazine-2(8H)-4(3H)-dione.
5'-CGTCGXTXTXGGCTC-3'        SEQ ID 37    44.3
3'-GCAGC*KAKAK*CCGAG-5'      SEQ ID 26    The letter "*K*" represents 2,6-diarnino-3-nitro-5-(1'-beta-D-2'-deoxyribofuranosyl)-pyridine; the letter "X" represents 2'-deoxyxanthosine.
5'-CGTCG*XTXTX*GGCTC-3'      SEQ ID 25    53.1
3'-GCAGC*KAKAK*CCGAG-5'      SEQ ID 26    The letter "*K*" represents 2,6-diarnino-3-nitro-5-(1'-beta-D-2'-deoxyribofuranosyl)-pyridine; the letter "*X*" represents 2'-deoxy-7-deazaxanthosine.
5'CGTCGXXXXXGGCTC-3'     SEQ ID 38    30.9
3'-GCAGCKKKKKCCGAG-5'        SEQ ID 39    The letter "K" represents 2,4-diamino-5-(1'-beta-D-2'-deoxyribofuranosyl)-pyrimidine; the letter "X" represents 8-(beta-D-2'-deoxyribofuranosyl)imidazo[1,2-a]-1,3,5-triazine-2(8H)-4(3H)-dione.
5'-CGTCG*XXXXX*GGCTC-3'      SEQ ID 40    51.4
31-GCAGCKKKKKCCGAG-5'        SEQ ID 39    The letter "K" represents 2,4-diamino-5-(1'-beta-D-2'-deoxyribofuranosyl)-pyrimidine; the letter "X" represents 2'-deoxyxanthosine.
5'-CGTCG*XXXXX*GGCTC-3'      SEQ ID 27    57.9
3'-GCAGCKKKKKCCGAG-5'        SEQ ID 39    The letter "K" represents 2,4-diamino-5-(1'-beta-D-2'-deoxyribofuranosyl)-pyrimidine; the letter "*X*" represents 2'-deoxy-7-deazaxanthosine.
5'-CGTCGXXXXXGGCTC-3'    SEQ ID 38    31.7
3'-GCAGC*KKKKK*CCGAG-5'      SEQ ID 28    The letter "*K*" represents 2,6-diarnino-3-nitro-5-(1'-beta-D-2'-deoxyribofuranosyl)-pyridine; the letter "X" represents 8-(β-D-2'-deoxyribofuranosyl)imidazo[1,2-a]-1,3,5-triazine-2(8H)-4(3H)-dione.
5'-CGTCG*XXXXX*GGCTC-3'      SEQ ID 40    44.7
3'-GCAGC*KKKK*CCGAG-5'       SEQ ID 28    The letter "*K*" represents 2,6-diarnino-3-nitro-5-(1'-beta-D-2'-deoxyribofuranosyl)-pyridine; the letter "X" represents 2'-deoxyxanthosine.
5'-CGTCG*XXXXX*GGCTC-3'      SEQ ID 27    57.9
3'-GCAGC*KKKKK*CCCGAG-5'     SEQ ID 28    The letter "*K*" represents 2,6-diarnino-3-nitro-5-(1'-beta-D-2'-deoxyribofuranosyl)-pyridine; the letter "*X*" represents 2'-deoxy-7-deazaxanthosine.

Example 5.2

Comparison of two implementations of the small donor-acceptor-donor hydrogen bonding pattern, on 2,4-diaminopyrimidine versus 2,6-diamino-3-nitropyridine, and two implementations of the large the hydrogen bonding heterocycle implementing the acceptor-donor-acceptor hydrogen bonding pattern, in Watson-Crick base pairs. Data are shown in Table 2, where K is 2,4-diaminopyrimidine, italicized K is 2,6-diamino-3-nitropyridine, X is xanthosine, bold X is triazine, and italicized X is 7-dezazxanthosine

Example 5.3

Melting temperatures of the reference duplex where the middle five base pairs are skinny. Here, the implementation of the acceptor-acceptor-donor (S) hydrogen bonding pattern is on pseudocytidine.

TABLE 3

Mispairing in the skinny series gives less stable duplexes than the hydrogen bond matched skinny pairs, showing molecular recognition and its specificity.

5'-CGTCGTTTTTGGCTC-3'      SEQ ID 3    38.1
3'-GCAGCAAZAACCGAG-5'      SEQ ID 6    The letter "Z" represents 6-amino-3-(2'-deoxy-D-ribofuranosyl)-5-nitro-1H-pyridin-2-one.

TABLE 3-continued

Mispairing in the skinny series gives less stable duplexes than the hydrogen bond matched skinny pairs, showing molecular recognition and its specificity.

| | | |
|---|---|---|
| 5'-CGTCGTTSTTGGCTC-3' | SEQ ID 13 | 47.2 |
| 3'-GCAGCAAZAACCGAG-5' | SEQ ID 6 | The letter "Z" represents 6-amino-3-(2'-deoxy-D-ribofuranosyl)-5-nitro-1H-pyridin-2-one. The letter "S" represents 4-amino-N1-methyl-5-(1'-beta-D-2'-deoxyribofuranosyl)-2(1H)-pyrimidinone. |
| 5'-CGTCGTSSSTGGCTC-3' | SEQ ID 15 | 54.1 |
| 3'-GCAGCAZZZACCGAG-5' | SEQ ID 8 | The letter "Z" represents 6-amino-3-(2'-deoxy-D-ribofuranosyl)-5-nitro-1H-pyridin-2-one. The letter "S" represents 4-amino-N1-methyl-5-(1'-beta-D-2'-deoxyribofuranosyl)-2(1H)-pyrimidinone. |
| 5'-CGTCGSTSTSGGCTC-3' | SEQ ID 17 | 50.1 |
| 3'-GCAGCZAZAZCCGAG-5' | SEQ ID 10 | The letter "Z" represents 6-amino-3-(2'-deoxy-D-ribofuranosyl)-5-nitro-1H-pyridin-2-one. The letter "S" represents 4-amino-N1-methyl-5-(1'-beta-D-2'-deoxyribauranosyl)-2(1H)-pyrimidinone. |
| 5'CGTCGTTTITGGCTC-3' | SEQ ID 3 | <20 |
| 3'-GCAGCZZZZZCCGAG-5' | SEQ ID 12 | The letter "Z" represents 6-amino-3-(2'-deoxy-D-ribofuranosyl)-5-nitro-1H-pyridin-2-one. |
| 5'-CGTCGTTSTTGGCTC-3' | SEQ ID 13 | <20 |
| 3'-GCAGCZZZZZCCGAG-5' | SEQ ID 12 | The letter "Z" represents 6-amino-3-(2'-deoxy-D-ribofuranosyl)-5-nitro-1H-pyridin-2-one. The letter "S" represents 4-amino-N1-methyl-5-(1'-beta-D-2'-deoxyribofuranosyl)-2(1H)-pyrimidinone. |
| 5'-CGTCGTSSSTGGCTC-3' | SEQ ID 15 | 37.4 |
| 3'-GCAGCZZZZZCCGAG-5' | SEQ ID 12 | The letter "Z" represents 6-amino-3-(2'-deoxy-D-ribofuranosyl)-5-nitro-1H-pyridin-2-one. The letter "S" represents 4-amino-N1-methyl-5-(1'-beta-D-2'-deoxyrihofuranosyl)-2(1H)-pyrimidinone. |
| 5'-CGTCGSTSTSGGCTC-3' | SEQ ID 17 | 36.3 |
| 3'-GCAGCZZZZZCCGAG-5' | SEQ ID 12 | The letter "Z" represents 6-amino-3-(2'-deoxy-D-ribofuranosyl)-5-nitro-1H-pyridin-2-one. The letter "S" represents 4-amino-N1-methyl-5-(1'-beta-D-2'-deoxyribofuranosyl)-2 (1H)-pyrimidinone . |
| 5'-CGTCGSSSSSGGCTC-3' | SEQ ID 19 | 60.9 |
| 3'-GCAGCZZZZZCCGAG-5' | SEQ ID 12 | The letter "Z" represents 6-amino-3-(2'-deoxy-D-2'-deoxyribofuranosyl)-5-nitro-1H-pyridin-2-one. The letter "S" represents 4-amino-N1-methyl-5-(1'-beta-D-2'-deoxyribofuranosyl)-2(1H)-pyrimidinone. |
| 5'-CGTCGTTTTTGGCTC-3' | SEQ ID 3 | 38.1 |
| 3'-GCAGCAAZAACCGAG-5' | SEQ ID 6 | The letter "Z" represents 6-amino-3(2'-deoxy-D-ribofuranosyl)-5-nitro-1H-pyridin-2-one . |
| 5'-CGTCGTTTTTGGCTC-3' | SEQ ID 3 | 45.9 |
| 3'-GCAGCAA*K*AACCGAG-5' | SEQ ID 22 | The letter "*K*" represents 2,6-diamino-3-nitro-5-(1'-beta-D-2'-deoxyribofuranosyl)-pyridine. |
| 5'-CGTCGTTSTTGGCTC-3' | SEQ ID 13 | 37.6 |
| 3'-GCAGCAA*K*AACCGAG-5' | SEQ ID 22 | The letter "*K*" represents 2,6-diamino-3-nitro-5-(1'-beta-D-2'-deoxyribofuranosyl)-pyridine. The letter "S" represents 4-amino-N1-methyl-5-(1'-beta-D-2'-deoxyribofuranosyl)-2(1H)-pyrimidinone. |
| 5'-CGTCGTTTTTGGCTC-3' | SEQ ID 3 | 48.0 |
| 3'-GCAGCA*KKK*ACCGAG-5' | SEQ ID 24 | The letter "*K*" represents 2,6-diamino-3-nitro-5-(1'-beta-D-2'-deoxyribofuranosyl)-pyridine. |
| 5'-CGTCGTSSSTGGCTC-3' | SEQ ID 15 | 29.4 |
| 3'-GCAGCA*KKK*ACCGAG-5' | SEQ ID 24 | The letter "*K*" represents 2,6-diamino-3-nitro-5-(1'-beta-D-2'-deoxyribofuranosyl)-pyridine. The letter "S" represents 4-amino-N1-methyl-5-(1'-beta-D-2'-deoxyribofurano syl)-2(1H)-pyrimidinone. |
| 5'-CGTCGTTTTTGGCTC-3' | SEQ ID 3 | 41.0 |
| 3'-GCAGC*KAKAK*CCGAG-5' | SEQ ID 26 | The letter "*K*" represents 2,6-diamino-3-nitro-5-(1'-beta-D-2'-deoxyribofuranosyl)-pyridine. |
| 5'-CGTCGTTTTTGGCTC-3' | SEQ ID 3 | 46.8 |
| 3'-GCAGC*KKKKK*CCGAG-5' | SEQ ID 28 | The letter "*K*" represents 2,6-diamino-3-nitro-5-(1'-beta-D-2'-deoxyribofuranosyl)-pyridine . |
| 5'-CGTCGTTSTTGGCTC-3' | SEQ ID 13 | 39.0 |
| 3'-GCAGC*KKKKK*CCGAG-5' | SEQ ID 28 | The letter "*K*" represents 2,6-diamino-3-nitro-5-(1'-beta-D-2'-deoxyribofuranosyl)-pyridine. The letter "S" represents 4-amino-N1-methyl-5-(1'-beta-D-2'-deoxyribofuranosyl)-2(1H)-pyrimidinone. |
| 5'-CGTCGTSSSTGGCTC-3' | SEQ ID 15 | 30.6 |
| 3'-GCAGC*KKKKK*CCGAG-5' | SEQ ID 28 | The letter "*K*" represents 2,6-diamino-3-nitro-5-(1'-beta-D-2'-deoxyribofuranosyl)-pyridine. The letter "S" represents 4-amino-N1-methyl-5-(1'-beta-D-2'-deoxyribofuranosyl)-2(1H)-pyrimidinone. |
| 5'-CGTCGSSSSSGGCTC-3' | SEQ ID 19 | <20 |
| 3'-GCAGC*KKKKK*CCGAG-5' | SEQ ID 28 | The letter "*K*" represents 2,6-diamino-3-nitro-5-(1'-beta-D-2'-deoxyribofuranosyl)-pyridine. The letter "S" represents 4-amino-N1-methyl-5-(1'-beta-D-2'-deoxyribofuranosyl)-2(1H)-pyrimidinone. |
| 5'-CGTCGTTTTTGGCTC-3' | SEQ ID 3 | <20 |
| 3'-GCAGCZ*K*Z*K*ZCCGAG-5' | SEQ ID 41 | The letter "*K*" represents 2,6-diamino-3-nitro-5-(1'-beta-D-2'-deoxyribofuranosyl)-pyridine. The letter "Z" represents 6-amino-3-(2'-deoxy-D-ribofuranosyl)-5-nitro-1H-pyridin-2-one. |
| 5'-CGTCGSTSTSGGCTC-3' | SEQ ID 17 | 58.0 |
| 3'-GCAGCZ*K*Z*K*ZCCGAG-5' | SEQ ID 41 | The letter "*K*" represents 2,6-diamino-3-nitro-5-(1'-beta-D-2'-deoxyribofuranosyl)-pyridine. The letter "Z" represents 6-amino-3-(2'-deoxy-D-ribofuranosyl)-5-nitro-1H-pyridin-2-one. The letter "S" represents 4-amino-N1-methyl-5-(1'-beta-D-2'-deoxyribofuranosyl)-2(1H)-pyrimidinone. |
| 5'-CGTCGSSSSSGGCTC-3' | SEQ ID 19 | 42.7 |

TABLE 3-continued

Mispairing in the skinny series gives less stable duplexes than the hydrogen bond matched skinny pairs, showing molecular recognition and its specificity.

3'-GCAGCZ*KZKZ*CCGAG-5'   SEQ ID 41   The letter "*K*" represents 2,6-diamino-3-nitro-5-(1'-beta-D-2'-deoxyribofuranosyl)-pyridine. The letter "Z" represents, 6-amino-3-(2'-deoxy-D-ribofuranosyl)-5-nitro-1H-pyridin-2-one. The letter "S" represents 4-amino-N1-methyl-5-(1'-beta-D-2'-deoxyribofuranosyl)-2(1H)-pyrimidinone.
5'-CGTCGTTTTTGGCTC-3'   SEQ ID 3   <20
3'-GCAGCTTTTTCCGAG-5'   SEQ ID 42   These are all standard nucleotides.
5'-CGTCGSSSSSGGCTC-3'   SEQ ID 19   <20
3'-GCAGCTTTTTCCGAG-5'   SEQ ID 42   The letter "S" represents 4-amino-N1-methyl-5-(1'-beta-D-2'-deoxyribofuranosyl)-2(1H)-pyrimidinone.

TABLE 4

Comparing different implementations of the K hydrogen bonding pattern.

5'-CGTCGTTTTTGGCTC-3'   SEQ ID 3   45.9
3'-GCAGCAA*K*AACCGAG-5' SEQ ID 30   The letter "K" represents 2,4-diamino-5-(1'-beta-D-2'-deoxyribofuranosyl)-pyrimidine.
5'-CGTCGTTTTTGGCTC-3'   SEQ ID 3   45.9
3'-GCAGCAA*K*AACCGAG-5' SEQ ID 22   The letter "*K*" represents 2,6-diamino-3-nitro-5-(1'-beta-D-2'-deoxyribofuranosyl)-pyridine.
5'-CGTCGTTTTTGGCTC-3'   SEQ ID 3   45.9
3'-GCAGCA*KKK*ACCGAG-5' SEQ ID 33   The letter "K" represents 2,4-diamino-5-(1'-beta-D-2'-deoxyribofuranosyl)-pyrimidine.
5'-CGTCGTTTTTGGCTC-3   SEQ ID 3   48.0
3'-GCAGCA*KKK*ACCGAG-5' SEQ ID 24   The letter "*K*" represents 2,6-diamino-3-nitro-5(1'-beta-D-2'-deoxyribofuranosyl)-pyridine.
5'-CGTCGTTTTTGGCTC-3'   SEQ ID 3   42.9
3'-GCAGC*K*A*K*A*K*CCGAG-5' SEQ ID 36   The letter "K" represents 2,4-diarnino-5-(1'-beta-D-2'-deoxyribofuranosyl)-pyrimidine.
5'-CGTCGTTTTTGGCTC-3'   SEQ ID 3   41.0
3'-GCAGC*KAKAK*CCGAG-5' SEQ ID 26   The letter "*K*" represents 2,6-diamino-3-nitro-5-(1'-beta-D-2'-deoxyribofuranosyl)-pyridine.
5'-CGTCGTTTTTGGCTC-3'   SEQ ID 3   41.0
3'-GCAGC*KKKKK*CCGAG-5' SEQ ID 39   The letter "K" represents 2,4-diamino-5-(1'-beta-D-2'-deoxyribofuranosyl)-pyrimidine.
5'CGTCGTTTTTGGCTC-3'   SEQ ID 3   46.8
3'-GCAGC*KKKKK*CCGAG-5' SEQ ID 28   The letter "*K*" represents 2,6-diamino-3-nitro-5-(1'-beta-D-2'-deoxyribofuranosyl)-pyridine.
5'-CGTCGSSSSSGGCTC-3'   SEQ ID 19 <20
3'-GCAGC*KKKKK*CCGAG-5' SEQ ID 39   The letter "K" represents 2,4-diarnino-5-(1'-beta-D-2'-deoxyribofuranosyl)-pyrimidine.
5'-CGTCGSSSSSGGCTC-3'   SEQ ID 19 <20
3'-GCAGC*KKKKK*CCGAG-5' SEQ ID 28   The letter "*K*" represents 2,6-diamino-3-nitro-5-(1'-beta-D-2'-deoxyribofuranosyl)-pyridine.

Example 5.4

Melting temperatures of duplexes consisting of only skinny base pairs, without Watson-Crick pairs at the ends of the species recognizing each other.

Measurements were made, as before, in 10 mM Na cacodylate (pH 6.8), 10 mM NaCl, and two micromolar of each oligonucleotide.

Watson-Crick Size Complementary Reference Sequences.

Duplex segment with molecular recognition involving 15 consecutive size complementary Watson-Crick pairs, as well known in the art. This serves as a reference sequence. D=diaminopurine. K=2,6-diamino-3-nitropyridine. Z is 6-amino-5-nitro-pyridin-2-one. X=7-deazaxanthosine. P=7-amino-9H-(imidazo[1,2-c]pyrimidin-5(1H)-one.

```
                                      SEQ ID 44
OligoPurine 1:      3'-XPP DPB XDD XXB DBD
```

Melting temperature=60.9° C.

The letter "D" represents 2'-deoxy-2-aminoadenosine.
The letter "P" represents 7-amino-9-(1'-beta-D-2'-deoxyribofuranosyl)-imidazo[1,2-c]pyrimidin-5(1H)-one.
The letter "X" represents 2'-deoxy-7-deazaxanthosine.
The letter "B" represents 4-amino-3-hydro-7-(2-deoxy-ß-D-ribofuranosyl)-pyrrolo[2,3-d]pyrimidin-2-one.
The letter "Z" represents 6-amino-3-(2'-deoxy-D-ribofuranosyl)-5-nitro-1H-pyridin-2-one.
The letter "K" represents 2,6-diamino-3-nitro-5-(1'-beta-D-2'-deoxyribofuranosyl)-pyridine.
The letter "S" represents 4-amino-N1-methyl-5-(1'-beta-D-2'-deoxyribofuranosyl)-2(1H)-pyrimidinone.

```
                                      SEQ ID 43
OligoPyrimidine 1:  5'-KZZ TZS KTT KKS TST SEQ ID 45
OligoPurine 2:      5'-DBB XBP DXX DDP XPX
```

-continued

```
                              SEQ ID 46
OligoPyrimidine 2:    3-TSS KSZ TKK TTZ KZK
```

Melting temperature=63.9° C.
The letter "D" represents 2'-deoxy-2-aminoadenosine.
The letter "P" represents 7-amino-9-(1'-beta-D-2'-deoxyribofuranosyl)-imidazo[1,2-c]pyrimidin-5(1H)-one.
The letter "X" represents 2'-deoxy-7-deazaxanthosine.
The letter "B" represents 4-amino-3-hydro-7-(2-deoxy-ß-D-ribofuranosyl)-pyrrolo[2,3-d]pyrimidin-2-one.
The letter "Z" represents 6-amino-3-(2'-deoxy-D-ribofuranosyl)-5-nitro-1H-pyridin-2-one.
The letter "K" represents 2,6-diamino-3-nitro-5-(1'-beta-D-2'-deoxyribofuranosyl)-pyridine.
The letter "S" represents 4-amino-N1-methyl-5-(1'-beta-D-2'-deoxyribofuranosyl)-2(1H)-pyrimidinone.
    Standard-Watson-Crick:
    This includes weaker A:T pairs.

```
                              SEQ ID 47
Standard Purine 1:      5'-AGA GAA AAA GGA GGA SEQ ID 48
Standard Pyrimidine 1:  3'-TCT CTT TTT CCT CCT
```

Melting temperature=36.5° C.
    Standard-Watson-Crick:
    This includes weaker A:T pairs.

```
                              SEQ ID 49
Standard Purine 2:      5'-AGG AGG AAA AAG AGA SEQ ID 50
Standard Pyrimidine 2:  3'-TCC TCC TTT TTC TCT
```

Melting temperature=34.8° C.
Duplex Segment with Molecular Recognition Involving 15 Consecutive "Skinny" Pairs.
    This is the rule-based molecular recognition system of the current invention. Note that the thermodynamic stability of this duplex, as measured by its melting temperature, is only slightly below that of the reference sequences.

```
                              SEQ ID 43
OligoPyrimidine 1:    5'-KZZ TZS KTT KKS TST SEQ ID 46
OligoPyrimidine 2:    3'-TSS KSZ TKK TTZ KZK
```

Melting temperature=58.3° C.
The letter "Z" represents 6-amino-3-(2'-deoxy-D-ribofuranosyl)-5-nitro-1H-pyridin-2-one.
The letter "K" represents 2,6-diamino-3-nitro-5-(1'-beta-D-2'-deoxyribofuranosyl)-pyridine.
The letter "S" represents 4-amino-N1-methyl-5-(1'-beta-D-2'-deoxyribofuranosyl)-2(1H)-pyrimidinone. Watson-Crick with Mispairs

```
                              SEQ ID 43
OligoPyrimidine 1:    5'-KZZ TZS KTT KKS TST SEQ ID 45
OligoPurine 2:        5'-DBB XBP DXX DDP XPX
```

Melting temperature <20° C.
The letter "D" represents 2'-deoxy-2-aminoadenosine.
The letter "P" represents 7-amino-9-(1'-beta-D-2'-deoxyribofuranosyl)-imidazo[1,2-c]pyrimidin-5(1H)-one.
The letter "X" represents 2'-deoxy-7-deazaxanthosine.
The letter "B" represents 4-amino-3-hydro-7-(2-deoxy-ß-D-ribofuranosyl)-pyrrolo[2,3-d]pyrimidin-2-one.
The letter "Z" represents 6-amino-3-(2'-deoxy-D-ribofuranosyl)-5-nitro-1H-pyridin-2-one.
The letter "K" represents 2,6-diamino-3-nitro-5-(1'-beta-D-2'-deoxyribofuranosyl)-pyridine.
The letter "S" represents 4-amino-N1-methyl-5-(1'-beta-D-2'-deoxyribofuranosyl)-2(1H)-pyrimidinone.

```
                              SEQ ID 46
OligoPyrimidine 2:    5'-KZK ZTT KKT ZSK SST SEQ ID 44
OligoPurine 1:        5'-DBD BXX DDX BPD PPX
```

Melting temperature <20° C.
The letter "D" represents 2'-deoxy-2-aminoadenosine.
The letter "P" represents 7-amino-9-(1'-beta-D-2'-deoxyribofuranosyl)-imidazo[1,2-c]pyrimidin-5(1H)-one.
The letter "X" represents 2'-deoxy-7-deazaxanthosine.
The letter "B" represents 4-amino-3-hydro-7-(2-deoxy-ß-D-ribofuranosyl)-pyrrolo[2,3-d]pyrimidin-2-one.
The letter "Z" represents 6-amino-3-(2'-deoxy-D-ribofuranosyl)-5-nitro-1H-pyridin-2-one.
The letter "K" represents 2,6-diamino-3-nitro-5-(1'-beta-D-2'-deoxyribofuranosyl)-pyridine.
The letter "S" represents 4-amino-N1-methyl-5-(1'-beta-D-2'-deoxyribofuranosyl)-2(1H)-pyrimidinone.
Single Stranded Melting Temperatures
    These show no folding.

```
                              SEQ ID 44
Fatty1-15:      5'-DBD BXX DDX BPD PPX
```

The letter "D" represents 2'-deoxy-2-aminoadenosine.
The letter "P" represents 7-amino-9-(1'-beta-D-2'-deoxyribofuranosyl)-imidazo[1,2-c]pyrimidin-5(1H)-one.
The letter "X" represents 2'-deoxy-7-deazaxanthosine.
The letter "B" represents 4-amino-3-hydro-7-(2-deoxy-ß-D-ribofuranosyl)-pyrrolo[2,3-d]pyrimidin-2-one.
Melting temperature <20° C.

```
                              SEQ ID 45
Fatty2-15:      5'-DBB XBP DXX DDP XPX
```

The letter "D" represents 2'-deoxy-2-aminoadenosine.
The letter "P" represents 7-amino-9-(1'-beta-D-2'-deoxyribofuranosyl)-imidazo[1,2-c]pyrimidin-5(1H)-one.
The letter "X" represents 2'-deoxy-7-deazaxanthosine.
The letter "B" represents 4-amino-3-hydro-7-(2-deoxy-ß-D-ribofuranosyl)-pyrrolo[2,3-d]pyrimidin-2-one.
Melting temperature <20° C.

```
                              SEQ ID 43
Skinny1-15:     5'-KZZ TZS KTT KKS TST
```

The letter "Z" represents 6-amino-3-(2'-deoxy-D-ribofuranosyl)-5-nitro-1H-pyridin-2-one.
The letter "K" represents 2,6-diamino-3-nitro-5-(1'-beta-D-2'-deoxyribofuranosyl)-pyridine.
The letter "S" represents 4-amino-N1-methyl-5-(1'-beta-D-2'-deoxyribofuranosyl)-2(1H)-pyrimidinone.
Melting temperature <20° C.

Skinny2-15:    5'-*KZK* ZTT *KK*T Z*SK* SST   SEQ ID 46

Melting temperature <20° C.
The letter "Z" represents 6-amino-3-(2'-deoxy)-D-ribofuranosyl)-5-nitro-1H-pyridin-2-one.

The letter "K" represents 2,6-diamino-3-nitro-5-(1'-beta-D-2'-deoxyribofuranosyl)-pyridine.

The letter "S" represents 4-amino-N1-methyl-5-(1'-beta-D-2'-deoxyribofuranosyl)-2(1H)-pyrimidinone.

---

What is claimed is:

1. A composition of matter, wherein said composition comprises one or more oligonucleotides, wherein two or more segments of said oligonucleotide(s) are composed entirely of nucleotides carrying heterocycles selected independently from the group consisting of

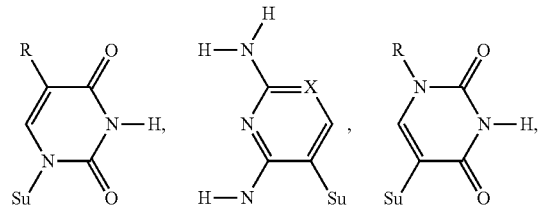

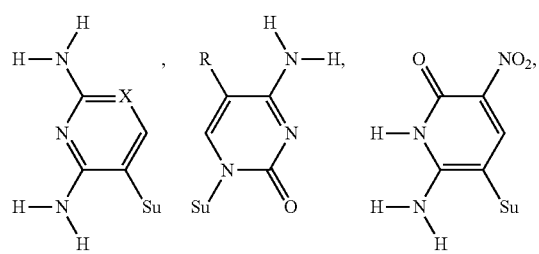

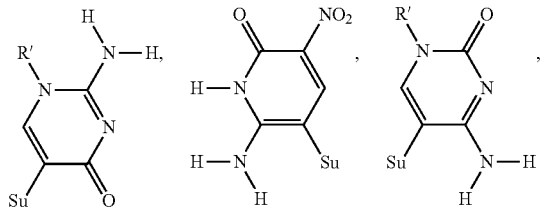

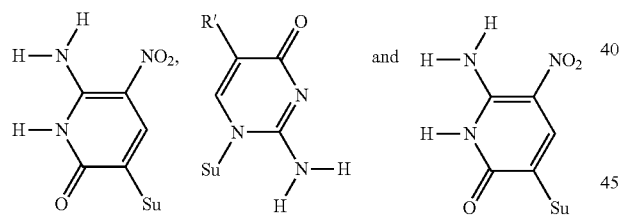

wherein Su indicates the point of attachment of said heterocycle to a sugar of the oligonucleotides, R' is $CH_3$, alkyl, alkenyl, alkynyl, or alkyl, alkenyl, or alkynyl carrying a functional group, wherein R=H, $CH_3$, alkyl, alkenyl, or alkynyl, or functionalized alkyl, alkenyl, or alkynyl, and X=N, C—$NO_2$, wherein said segments form one or more duplex regions, wherein said segments within said duplex region(s) are joined by skinny pairs, wherein

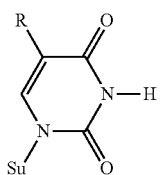

is paired with

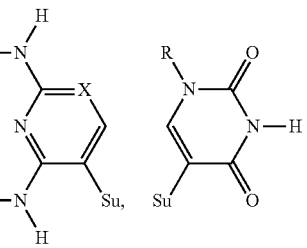

is paired with

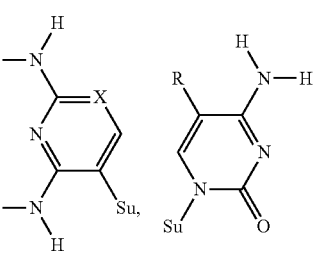

is paired with

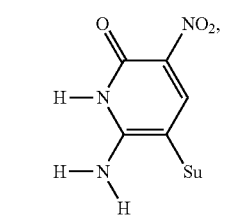

is paired with

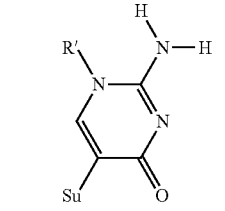

is paired with

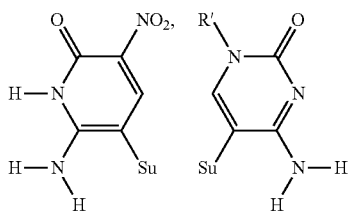

is paired with
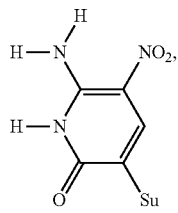
and
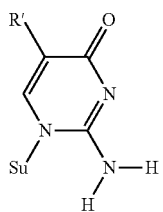
is paired with
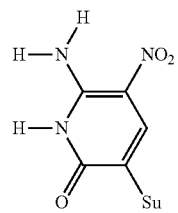
and wherein said duplex region comprises at least three pairs.
2. The compositions of claim 1, wherein said functional group is an amino group or a thiol group.
3. The composition of claim 1, wherein said heterocycles are independently selected from the group consisting of
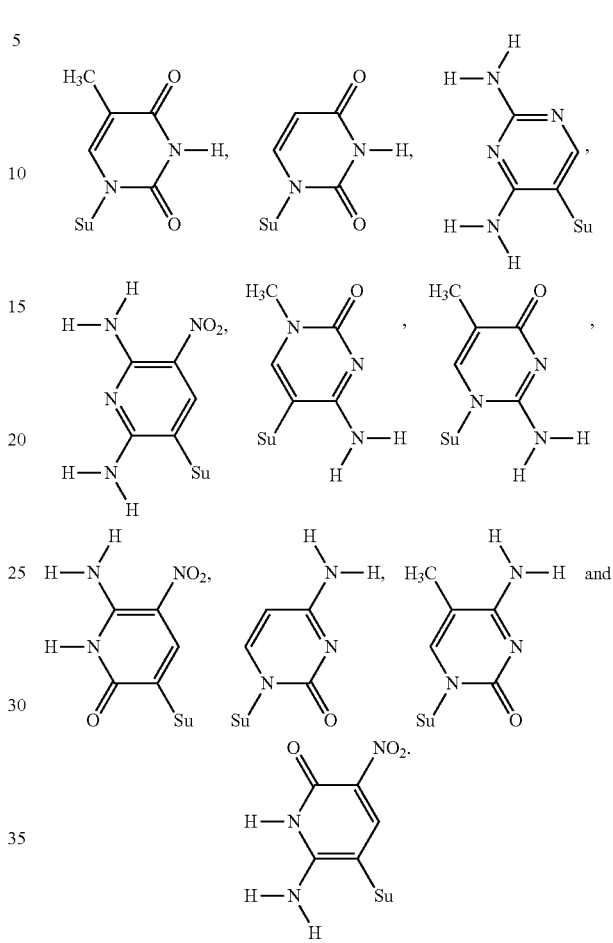
* * * * *